US007461968B2

(12) United States Patent
Demers et al.

(10) Patent No.: US 7,461,968 B2
(45) Date of Patent: Dec. 9, 2008

(54) SYSTEM, DEVICE, AND METHOD FOR MIXING LIQUIDS

(75) Inventors: Jason A. Demers, Manchester, NH (US); David W. McGill, Bedford, NH (US); Larry B. Gray, Merrimack, NH (US)

(73) Assignee: Deka Products Limited Partnership, Manchester, NH (US)

( * ) Notice: Subject to any disclaimer, the term of this patent is extended or adjusted under 35 U.S.C. 154(b) by 0 days.

(21) Appl. No.: 10/696,893

(22) Filed: Oct. 30, 2003

(65) Prior Publication Data

US 2005/0094485 A1 May 5, 2005

(51) Int. Cl.
*B01F 5/00* (2006.01)
*B01F 15/02* (2006.01)
(52) U.S. Cl. .............. 366/152.1; 366/160.2; 366/167.1; 366/182.2; 366/275; 137/3
(58) Field of Classification Search .............. 366/152.4, 366/182.2, 162.2, 167.1, 173.1, 152.1, 152.2, 366/160.2, 262, 275; 137/3
See application file for complete search history.

(56) References Cited

U.S. PATENT DOCUMENTS

| 1,133,254 | A | 3/1915 | Backus | |
|---|---|---|---|---|
| 1,664,576 | A | 4/1928 | Stuart et al. | |
| 1,792,906 | A | 2/1931 | Heilos | 251/209 |
| 2,313,551 | A | 3/1943 | Hurlbut | 417/387 |
| 2,525,251 | A | 10/1950 | Willard | 449/17 |
| 2,526,017 | A | 10/1950 | Figg | 251/209 |
| 2,703,055 | A | 3/1955 | Veth et al. | 417/205 |
| 2,776,854 | A | 1/1957 | Billstrom | 292/256 |
| 2,834,504 | A | 5/1958 | Annrcq | 220/211 |
| 2,902,253 | A | 9/1959 | Page | 251/209 |
| 3,048,121 | A | 8/1962 | Sheesley | 417/394 |
| 3,339,956 | A | 9/1967 | Bencene | 292/127 |

(Continued)

FOREIGN PATENT DOCUMENTS

WO    WO 87/06119    10/1987

(Continued)

OTHER PUBLICATIONS

Authorized Officer Ellen Elskamp, *The International Search Report and the Written Opinion of the International Searching Authority*, International Searching Authority, Jun. 14, 2005, 21 pages.

(Continued)

*Primary Examiner*—Tony G Soohoo
(74) *Attorney, Agent, or Firm*—Michelle Saquer Temple

(57) ABSTRACT

A system, device, and method for mixing liquids involves pumping a first liquid into a first pump chamber of a pumping apparatus through a channel of the pumping apparatus and pumping a second liquid from a second pump chamber of the pumping apparatus into either the channel or the first pump chamber, preferably while the first liquid is being pumped into the first pump chamber, so that the two liquids are mixed within the pumping apparatus. The second liquid is preferably pumped in a pulsatile mode in which small quantities of the second liquid are pumped at intervals. The quantity and/or the interval can be dynamically adjusted to result in a predetermined concentration of the two liquids. The contents of the first pump chamber are pumped to a receptacle.

11 Claims, 33 Drawing Sheets

U.S. PATENT DOCUMENTS

| | | | |
|---|---|---|---|
| 3,449,864 A | 6/1969 | Prost-Dame et al. | 49/477.1 |
| 3,481,076 A | 12/1969 | Bedard | 49/279 |
| 3,540,694 A | 11/1970 | Cornelius | 251/209 |
| 3,570,486 A | 3/1971 | Engelsher et al. | 128/218 |
| 3,722,858 A | 3/1973 | Sugimoto et al. | 251/209 |
| 3,727,882 A | 4/1973 | Burris et al. | 251/209 |
| 3,814,548 A | 6/1974 | Rupp | 417/395 |
| 3,856,338 A | 12/1974 | Johnsson | 292/256 |
| 4,072,934 A | 2/1978 | Hiller et al. | 340/243 |
| 4,073,521 A | 2/1978 | Mena | 292/256.65 |
| 4,093,176 A | 6/1978 | Contastin | 249/167 |
| 4,161,264 A * | 7/1979 | Malmgren et al. | 222/135 |
| 4,212,589 A | 7/1980 | Bosio | 417/12 |
| 4,230,300 A | 10/1980 | Wiltse | 251/205 |
| 4,247,018 A | 1/1981 | Credle | 222/1 |
| 4,431,425 A | 2/1984 | Thompson et al. | 604/246 |
| 4,468,219 A | 8/1984 | George et al. | 604/67 |
| 4,479,760 A | 10/1984 | Bilstad et al. | 417/375 |
| 4,479,761 A | 10/1984 | Bilstad et al. | 417/395 |
| 4,479,762 A | 10/1984 | Bilstad et al. | 417/395 |
| 4,576,211 A | 3/1986 | Valentini et al. | 141/329 |
| 4,634,430 A | 1/1987 | Polaschegg | 604/141 |
| 4,648,868 A | 3/1987 | Hardwick et al. | 604/32 |
| 4,650,339 A | 3/1987 | Chetcuti et al. | 366/142 |
| 4,662,540 A | 5/1987 | Schroter | 222/55 |
| 4,662,829 A * | 5/1987 | Nehring | 417/395 |
| 4,667,927 A | 5/1987 | Oscarsson | 251/209 |
| 4,696,671 A | 9/1987 | Epstein et al. | 604/67 |
| 4,698,160 A | 10/1987 | Haraguchi | 210/647 |
| 4,718,447 A | 1/1988 | Marshall | 137/268 |
| 4,721,138 A | 1/1988 | Simonazzi | 141/150 |
| 4,778,451 A | 10/1988 | Kamen | 604/67 |
| 4,798,580 A | 1/1989 | DeMeo et al. | 604/60 |
| 4,798,589 A * | 1/1989 | Tseo | 604/152 |
| 4,804,366 A | 2/1989 | Zdeb et al. | 604/85 |
| 4,807,660 A | 2/1989 | Aslanian | 137/382 |
| 4,808,161 A | 2/1989 | Kamen | 604/67 |
| 4,818,186 A | 4/1989 | Pastrone et al. | 417/63 |
| 4,826,482 A | 5/1989 | Kamen | 604/67 |
| 4,828,543 A * | 5/1989 | Weiss et al. | 604/6.09 |
| 4,833,922 A | 5/1989 | Frick et al. | 73/756 |
| 4,850,978 A | 7/1989 | Dudar et al. | 604/201 |
| 4,855,714 A | 8/1989 | Clarkson et al. | 340/521 |
| 4,857,048 A * | 8/1989 | Simons et al. | 604/503 |
| 4,925,444 A | 5/1990 | Orkin et al. | 604/250 |
| 4,927,198 A | 5/1990 | Fennell et al. | 292/306 |
| 4,976,162 A | 12/1990 | Kamen | 73/865.9 |
| 5,005,604 A | 4/1991 | Aslanian | 137/556 |
| 5,006,050 A | 4/1991 | Cooke et al. | 417/478 |
| 5,045,068 A | 9/1991 | Kawai et al. | 604/246 |
| 5,051,922 A | 9/1991 | Toral et al. | 364/510 |
| 5,062,774 A | 11/1991 | Kramer et al. | 417/413 |
| 5,069,792 A | 12/1991 | Prince et al. | 210/627 |
| 5,088,515 A | 2/1992 | Kamen | 137/15 |
| 5,098,262 A | 3/1992 | Wecker et al. | 417/395 |
| 5,098,371 A | 3/1992 | Juji et al. | 604/4 |
| 5,113,904 A | 5/1992 | Aslanian | 137/556 |
| 5,116,316 A | 5/1992 | Sertic et al. | 604/83 |
| 5,122,116 A | 6/1992 | Kriesel et al. | 604/89 |
| 5,146,414 A | 9/1992 | McKown et al. | 364/510 |
| 5,147,313 A * | 9/1992 | Dikeman | 604/153 |
| 5,150,796 A | 9/1992 | Pierson | 209/370 |
| 5,156,186 A | 10/1992 | Manska | 137/556 |
| 5,165,869 A * | 11/1992 | Reynolds | 417/385 |
| 5,167,837 A | 12/1992 | Snodgrass et al. | 210/767 |
| 5,178,182 A | 1/1993 | Kamen | 137/454.2 |
| 5,186,333 A | 2/1993 | Pierson et al. | 209/370 |
| 5,188,455 A * | 2/1993 | Hammerstedt | 366/177.1 |
| 5,197,787 A | 3/1993 | Matsuda et al. | 303/10 |
| 5,255,072 A | 10/1993 | Mikasa et al. | 356/432 |
| 5,267,956 A * | 12/1993 | Beuchat | 604/30 |
| 5,272,646 A | 12/1993 | Farmer | 364/509 |
| 5,279,504 A | 1/1994 | Williams | 417/395 |
| 5,290,076 A | 3/1994 | Smith | 292/25 |
| 5,292,306 A | 3/1994 | Wynkoop et al. | 604/51 |
| 5,294,157 A | 3/1994 | Smith et al. | 292/25 |
| 5,302,093 A | 4/1994 | Owens et al. | 417/474 |
| 5,325,884 A | 7/1994 | Mirel et al. | 137/110 |
| 5,330,426 A | 7/1994 | Kriesel et al. | 604/89 |
| 5,336,053 A | 8/1994 | Wynkoop | 417/53 |
| D350,823 S | 9/1994 | Lanigan | D24/111 |
| 5,350,357 A | 9/1994 | Kamen et al. | 604/29 |
| 5,351,686 A | 10/1994 | Steuer et al. | 600/310 |
| 5,355,890 A | 10/1994 | Aguirre et al. | 128/680 |
| 5,378,126 A | 1/1995 | Abrahamson et al. | 417/479 |
| 5,384,714 A | 1/1995 | Kidd | 702/51 |
| 5,385,540 A | 1/1995 | Abbott et al. | 604/4 |
| 5,401,059 A | 3/1995 | Ferrario | 283/67 |
| 5,408,420 A | 4/1995 | Slocum et al. | 702/51 |
| 5,411,472 A | 5/1995 | Steg et al. | 604/4 |
| 5,421,823 A | 6/1995 | Kamen et al. | 604/28 |
| 5,423,738 A | 6/1995 | Robinson et al. | 604/601 |
| 5,428,527 A | 6/1995 | Niemi | 364/152 |
| 5,429,485 A * | 7/1995 | Dodge | 417/442 |
| 5,431,626 A | 7/1995 | Bryant et al. | 604/65 |
| 5,438,510 A | 8/1995 | Bryant et al. | 364/413.11 |
| 5,439,355 A | 8/1995 | Jimison et al. | 417/63 |
| 5,463,228 A | 10/1995 | Krause | 250/577 |
| 5,474,683 A | 12/1995 | Bryant et al. | 210/646 |
| 5,478,337 A | 12/1995 | Okamoto et al. | 604/413 |
| 5,482,440 A | 1/1996 | Dennehey et al. | 417/63 |
| 5,558,255 A | 9/1996 | Sancoff et al. | 222/189.06 |
| 5,575,310 A | 11/1996 | Kamen et al. | 137/614.11 |
| 5,578,012 A | 11/1996 | Kamen et al. | 604/151 |
| 5,579,244 A | 11/1996 | Brown | 364/558 |
| 5,584,671 A | 12/1996 | Schweitzer, Jr. et al. | 417/298 |
| 5,588,816 A | 12/1996 | Abbott et al. | 417/479 |
| 5,593,290 A * | 1/1997 | Greisch et al. | 417/478 |
| 5,628,908 A | 5/1997 | Kamen et al. | 210/646 |
| 5,634,896 A | 6/1997 | Bryant et al. | 604/29 |
| 5,638,737 A | 6/1997 | Mattson et al. | 92/101 |
| 5,647,391 A * | 7/1997 | Chan et al. | 366/152.4 |
| 5,649,810 A | 7/1997 | Schweitzer, Jr. et al. | 417/298 |
| 5,651,775 A | 7/1997 | Walker et al. | 604/207 |
| 5,681,285 A | 10/1997 | Ford et al. | 604/151 |
| 5,713,865 A | 2/1998 | Manning et al. | 604/122 |
| 5,716,343 A | 2/1998 | Kriesel et al. | 604/132 |
| 5,718,569 A * | 2/1998 | Holst | 417/479 |
| 5,755,683 A | 5/1998 | Houle et al. | 604/30 |
| 5,772,899 A * | 6/1998 | Snodgrass et al. | 210/767 |
| 5,776,103 A | 7/1998 | Kriesel et al. | 604/132 |
| 5,795,328 A | 8/1998 | Barnitz et al. | 604/67 |
| 5,808,181 A | 9/1998 | Wamsiedler et al. | 210/646 |
| 5,816,779 A | 10/1998 | Lawless et al. | 417/63 |
| 5,823,026 A | 10/1998 | Finke | 70/276 |
| 5,837,905 A * | 11/1998 | Strauss et al. | 73/861.63 |
| 5,868,162 A | 2/1999 | Dickerson, Jr. | 137/557 |
| 5,879,328 A | 3/1999 | Holmberg et al. | 604/82 |
| 5,883,299 A | 3/1999 | Green et al. | 417/63 |
| 5,935,105 A | 8/1999 | Manning et al. | 604/122 |
| 5,938,634 A | 8/1999 | Packard | 604/29 |
| 5,965,821 A | 10/1999 | Grudzien | 73/724 |
| 5,989,423 A | 11/1999 | Kamen et al. | 210/258 |
| 6,022,483 A | 2/2000 | Aral | 216/59 |
| 6,041,801 A | 3/2000 | Gray et al. | 137/14 |
| 6,065,941 A | 5/2000 | Gray et al. | 417/63 |
| 6,070,761 A | 6/2000 | Bloom et al. | 222/81 |
| 6,109,881 A | 8/2000 | Snodgrass et al. | 417/53 |
| 6,136,586 A | 10/2000 | Budowsky | 435/238 |
| 6,210,361 B1 | 4/2001 | Kamen et al. | 604/82 |
| 6,223,130 B1 | 4/2001 | Gray et al. | 702/51 |
| 6,234,997 B1 * | 5/2001 | Kamen et al. | 604/131 |
| 6,245,570 B1 | 6/2001 | Grimm et al. | 436/55 |
| 6,264,458 B1 | 7/2001 | Marcuz et al. | 425/451.9 |

| | | | |
|---|---|---|---|
| 6,343,614 B1 | 2/2002 | Gray et al. | 137/14 |
| 6,364,857 B1 | 4/2002 | Gray et al. | 604/153 |
| 6,382,923 B1 | 5/2002 | Gray | 417/53 |
| 6,416,293 B1 | 7/2002 | Bouchard et al. | 417/53 |
| 6,464,667 B1 | 10/2002 | Kamen et al. | 604/131 |
| 6,485,263 B1 | 11/2002 | Bryant et al. | 417/53 |
| 6,503,062 B1 | 1/2003 | Gray et al. | 417/53 |
| 6,520,747 B2 | 2/2003 | Gray et al. | 417/63 |
| 6,527,758 B2 | 3/2003 | Ko | |
| 6,604,908 B1 | 8/2003 | Bryant et al. | 417/26 |
| 6,663,359 B2 | 12/2003 | Gray et al. | 417/383 |
| 7,011,742 B2 | 3/2006 | Rosiello | 210/109 |
| 2003/0229302 A1 | 12/2003 | Robinson et al. | 604/4.01 |

FOREIGN PATENT DOCUMENTS

| WO | WO 94/22566 | 10/1994 |
|---|---|---|
| WO | WO 99/10028 | 3/1999 |
| WO | WO 01/18396 A1 | 3/2001 |
| WO | WO 03/086509 A1 | 10/2003 |

OTHER PUBLICATIONS

Authorized Officer Ellen Elskamp, *The International Search Report and the Written Opinion of the International Searching Authority*, International Searching Authority, Apr. 4, 2005, 13 pages.

Authorized Officer Ellen Elskamp, *Invitation to Pay Additional Fees /Communication Relating to the Results of the Partial International Search*, International Searching Authority, May 3, 2005, 7 pages.

\* cited by examiner

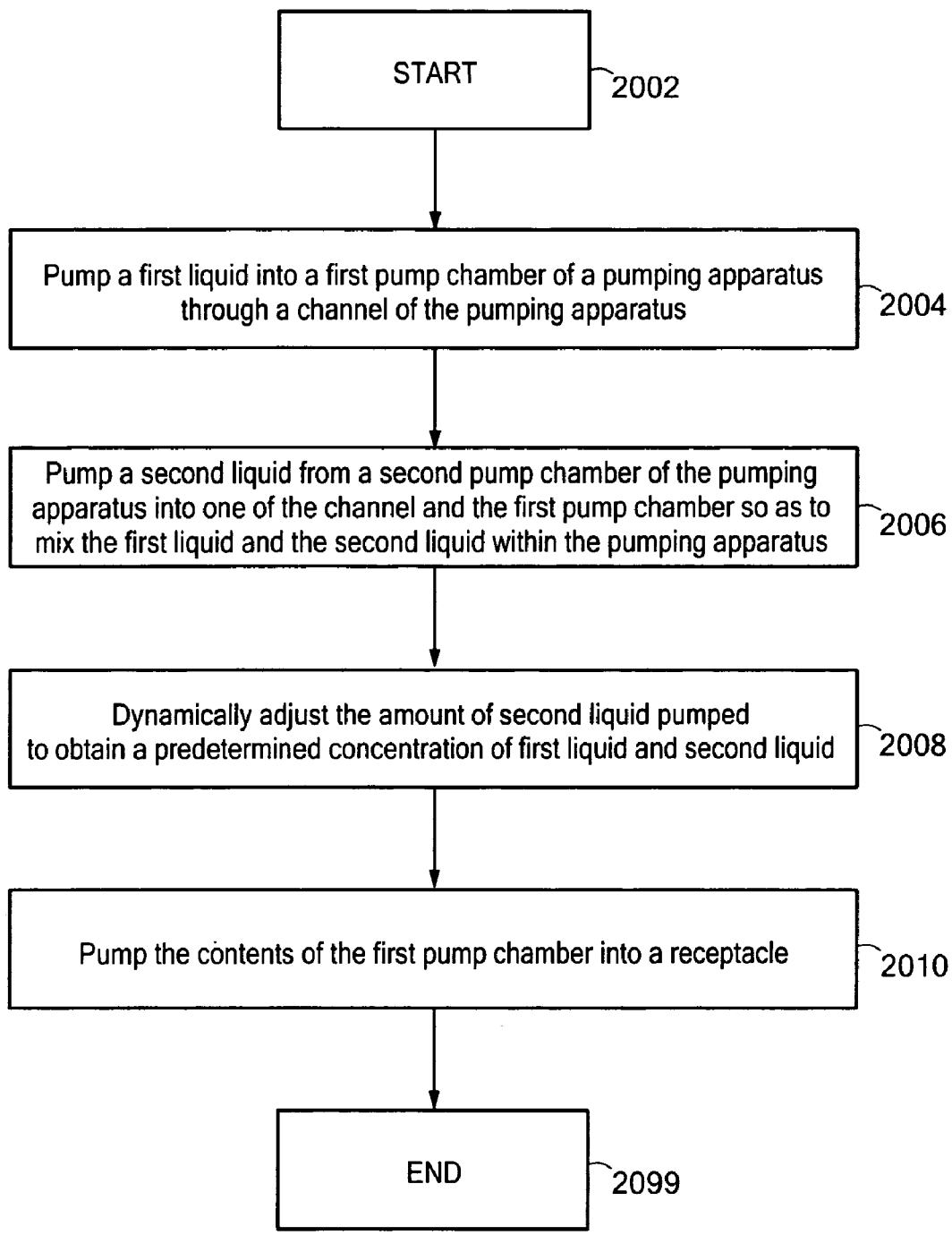
FIG. 20     2000

SYSTEM, DEVICE, AND METHOD FOR MIXING LIQUIDS

CROSS-REFERENCE TO RELATED APPLICATION(S)

The present application may include subject matter related to one or more of the following commonly-owned United States patent applications, each of which was filed on even date herewith and is hereby incorporated herein by reference in its entirety: U.S. patent application Ser. No. 10/696,969 entitled SYSTEM, DEVICE, AND METHOD FOR MIXING A SUBSTANCE WITH A LIQUID (referred to herein as "Application D70"); U.S. patent application Ser. No. 10/696,818, now U.S. Pat. No. 7,086,700 entitled TWO-STAGE MIXING SYSTEM, APPARATUS, AND METHOD (referred to herein as "Application D72"); U.S. patent application Ser. No. 10/697,176 entitled SYSTEM AND METHOD FOR PUMPING FLUID USING A PUMP CASSETE (referred to herein as "Application D73"); U.S. patent application Ser. No. 10/696,984 entitled DOOR LOCKING MECHANISM (referred to herein as "Application D74"); U.S. patent application Ser. No. 10/697,450 entitled BEZEL ASSEMBLY FOR PNEUMATIC CONTROL (referred to herein as "Application D75"); U.S. patent application Ser. No. 10/697,862 entitled PUMP CASSETE WITH SPIKING ASSEMBLY (referred to herein as "Application D84"); and U.S. patent application Ser. No. 10/696,990 entitled PUMP CASSETTE BANK (referred to herein as "Application D85").

FIELD OF THE INVENTION

The present invention relates generally to pumping liquids, and more particularly to a system, device, and method for mixing liquids.

BACKGROUND OF THE INVENTION

Millions of people receive blood transfusions each year. Although helpful in many cases, blood transfusions have associated risks. Among others, there is a risk that microorganisms capable of causing disease (i.e., pathogens) could pass from the donor blood to the ultimate blood recipient. For example, untreated blood used in a blood transfusion could have pathogens causing the West Nile Virus, or AIDS. It thus is critical for the public health to ensure that transfused blood is substantially free of pathogens.

The medical community has responded to this need by developing various techniques for removing known and unknown pathogens from donated blood. One technique involves mixing precise amounts of a diluted anti-pathogen compound with blood. Some time after mixing, a rinsing process removes the anti-pathogen compound from the blood. One complexity with this process, however, is the fact that the diluted anti-pathogen compound has a very short shelf life (e.g., on the order of about four hours). Accordingly, the diluted anti-pathogen compound must be produced a relatively short time before it is mixed with blood.

The anti-pathogen compound is not easy to handle before it is diluted. To the contrary, it has a very high pH (e.g., on the order of 11.0 or higher) and thus, is highly caustic and toxic. Mere contact with the undiluted solution can melt plastic, or burn flesh. Because of these undesirable properties, the undiluted solution typically is manually diluted by highly trained laboratory technicians that necessarily must be protected from direct contact with it. Consequently, laboratory technicians often are required to wear relatively impermeable protective gear while diluting the solution behind a chemical laminar flowhood. Such a process, however, is inherently slow, imprecise, and costly due to the multitude of safety requirements. Moreover, even with safeguards, diluting the undiluted solution still poses a risk to the laboratory technician.

SUMMARY OF THE INVENTION

In accordance with one aspect of the invention, mixing liquids involves pumping a first liquid into a first pump chamber of a pumping apparatus through a channel of the pumping apparatus and pumping a second liquid from a second pump chamber of the pumping apparatus into either the channel or the first pump chamber, preferably while the first liquid is being pumped into the first pump chamber, so that the two liquids are mixed within the pumping apparatus. The second liquid is preferably pumped in a pulsatile mode in which small quantities of the second liquid are pumped at intervals. The quantity and/or the interval can be dynamically adjusted to result in a predetermined concentration of the two liquids. The contents of the first pump chamber are pumped to a receptacle.

In accordance with another aspect of the invention, a method for mixing a first liquid with a second liquid involves pumping a first liquid into a first pump chamber of a pumping apparatus through a channel of the pumping apparatus and pumping a quantity of a second liquid from a second pump chamber of the pumping apparatus into one of the channel and the first pump chamber so as to mix the first liquid and the second liquid within the pumping apparatus. The quantity of the second liquid is preferably pumped during the pumping of the first liquid. The pumping apparatus may be a pneumatically operated pump cassette having various pneumatically operated pump chambers and valves. The second liquid may be pumped in a pulsatile mode. The pulse width and pulse interval may be dynamically adjusted to obtain a predetermined concentration of first liquid and second liquid. The contents of the first pump chamber may be pumped to a receptacle.

In accordance with another aspect of the present invention, an apparatus for mixing a first liquid with a second liquid includes a first pump controller operatively coupled to pump a first liquid into a first pump chamber of a pumping apparatus through a channel of the pumping apparatus and a second pump controller operatively coupled to pump a quantity of a second liquid from a second pump chamber of the pumping apparatus into one of the channel and the first pump chamber so as to mix the first liquid and the second liquid within the pumping apparatus. The quantity of the second liquid is preferably pumped during the pumping of the first liquid. The pumping apparatus may be a pneumatically operated pump cassette having various pneumatically operated pump chambers and valves. The second liquid may be pumped in a pulsatile mode. The pulse width and pulse interval may be dynamically adjusted to obtain a predetermined concentration of first liquid and second liquid. The contents of the first pump chamber may be pumped to a receptacle. The apparatus may include a pump cassette interface for pneumatically operating the chambers and valves of the pump cassette. The pump cassette interface may include a limiter for limiting the amount of second liquid held by the second pump chamber.

In accordance with another aspect of the present invention, an apparatus for mixing a first liquid with a second liquid includes means for pumping a first liquid into a first pump chamber of a pumping apparatus through a channel of the pumping apparatus and means for pumping a quantity of a second liquid from a second pump chamber of the pumping apparatus into one of the channel and the first pump chamber so as to mix the first liquid and the second liquid within the pumping apparatus.

In accordance with another aspect of the present invention, a system for mixing a first liquid with a second liquid includes a plurality of first liquid containers, each containing a first liquid; a second liquid container containing a second liquid; and a plurality of pumps, each pump operatively coupled to mix first liquid from a respective one of the plurality of first liquid containers with second liquid from the second liquid container. The system may also include a process controller in communication with the plurality of pumps for coordinating said mixing by the pumps.

In accordance with another aspect of the invention, red blood cell concentrate is mixed with an anti-pathogen solution to form an incubation solution.

BRIEF DESCRIPTION OF THE DRAWINGS

In the accompanying drawings:

FIG. 20 shows a logic flow diagram showing exemplary logic 2000 for mixing two liquids in accordance with an embodiment of the present invention.

DETAILED DESCRIPTION OF A PREFERRED EMBODIMENT

Figure 1A:
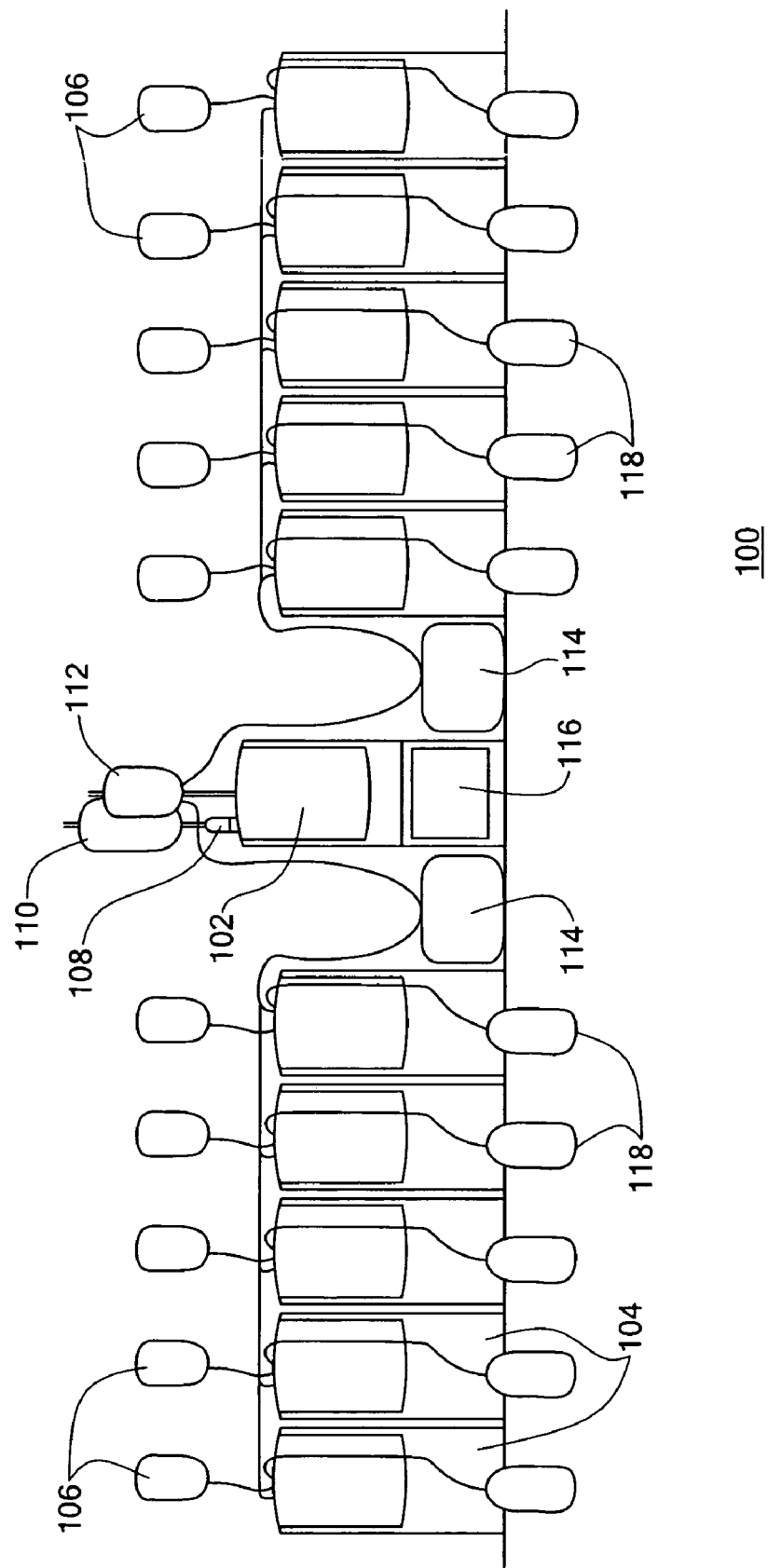
FIG. 1A shows an exemplary blood processing system having a plurality of blood pumps in accordance with an embodiment of the present invention.

Embodiments of the present invention provide for safely and efficiently mixing two liquids. In order to mix two liquids, a first liquid is pumped into a first pump chamber of a pumping apparatus through a channel of the pumping apparatus. A second liquid is pumped from a second pump chamber of the pumping apparatus into either the channel or the first pump chamber, preferably while the first liquid is being pumped into the first pump chamber. In this way, the two liquids are mixed within the pumping apparatus, and, more specifically, within the channel and/or the first pump chamber of the pumping apparatus. The second liquid is preferably pumped in a pulsatile mode in which small quantities of the second liquid are pumped at intervals, for example, as described in U.S. Pat. No. 6,604,908, which is hereby incorporated herein by reference in its entirety. The quantity and/or the interval can be dynamically adjusted to result in a predetermined concentration of the two liquids. The contents of the first pump chamber are pumped to a receptacle.

FIG. 20 is a logic flow diagram showing exemplary logic 2000 for mixing two liquids in accordance with an embodiment of the present invention. Beginning in block 2002, the logic pumps a first liquid into a first pump chamber of a pumping apparatus through a channel of the pumping apparatus, in block 2004. The logic pumps a second liquid from a second pump chamber of the pumping apparatus into one of the channel and the first pump chamber so as to mix the first liquid and the second liquid within the pumping apparatus, in block 2006. The logic dynamically adjusts the amount of second liquid pumped to obtain a predetermined concentration of first liquid and second liquid, in block 2008. The logic pumps the contents of the first pump chamber into a receptacle, in block 2010. The various pumping and adjusting operations may be repeated as necessary to process a predetermined quantity of liquids. The logic 2000 ends in block 2099.

In exemplary embodiments of the present invention, the pumping apparatus is a disposable pump cassette. The pump cassette typically includes two pump chambers and various valves. The pump chambers and valves are preferably operated pneumatically.

In exemplary embodiments of the present invention, an anti-pathogen solution is mixed with a red blood cell concentrate (RBCC) to form an incubation solution for reducing pathogens in the RBCC. The anti-pathogen solution is prepared by mixing a caustic anti-pathogen compound known as PEN110 or INACTINE, which is an organic solvent with a pH over 11 that is distributed by V.I. Technologies, Inc. of Watertown, Mass., with a buffer solution of sodium phosphate to a predetermined concentration (e.g., 1 part anti-pathogen compound to 99 parts buffer solution), preferably as described in Application D70. For convenience, this mixing of anti-pathogen compound with buffer solution may be referred to hereinafter as "compounding," and an apparatus that performs such compounding may be referred to hereinafter as a "compounder" or "compounder pump." The incubation solution is prepared by mixing the anti-pathogen solution with the RBCC to a predetermined concentration (e.g., 1 part anti-pathogen solution to 9 parts RBCC), as described below. For convenience, this mixing of anti-pathogen solution with RBCC may be referred to hereinafter as "blood processing," and an apparatus that performs such blood processing may be referred to hereinafter as a "blood pump."

System Overview

FIG. 1A shows an exemplary blood processing system 100 having a plurality of blood pumps in accordance with an embodiment of the present invention. Among other things, the blood processing system 100 includes a single compounder pump 102 and ten essentially identical blood pumps 104 organized as two banks of five blood pumps each. The compounder pump 102 pumps buffer solution from a buffer solution container 110 into a vial of anti-pathogen compound 108. The mixture, referred to as a working solution, is pumped into a working solution container 112. Each of the blood pumps 104 mixes working solution from the working solution container 112 with red blood cell concentrate (RBCC) from a RBCC container 106 to form an incubation solution that is pumped into an incubation bag 118. The incubation solution is typically allowed to incubate for some period of time, after which it is rinsed to remove the anti-pathogen compound to produce a pathogen reduced blood product. The blood processing system 100 typically also includes two sterile docks 114 that are used by the operator to splice together plastic tubing as necessary for various blood processing operations. The blood processing system 100 is controlled through a user interface 116.

Figure 1B:
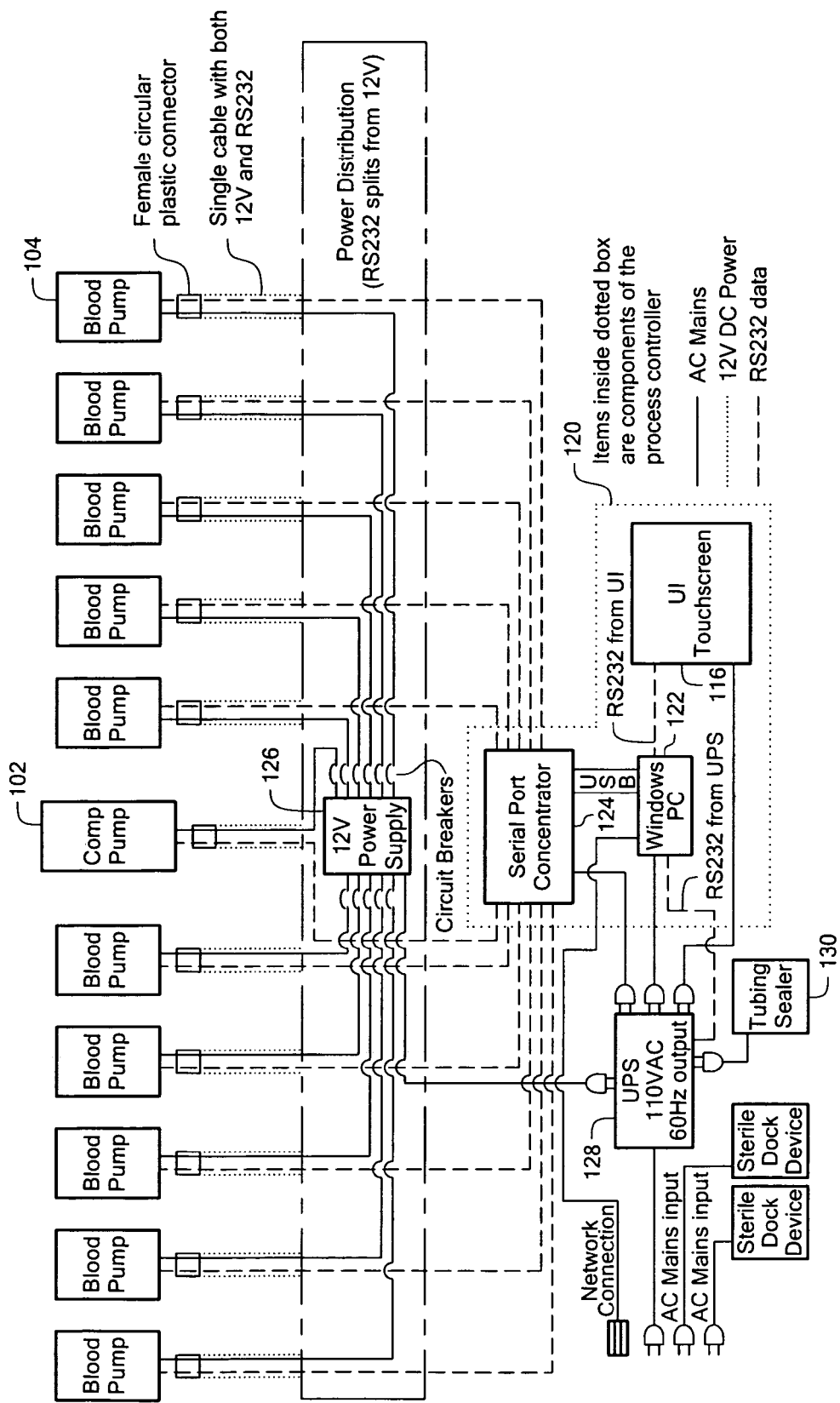
FIG. 1B shows an exemplary wiring diagram for one embodiment of the blood processing system shown in FIG. 1A.

FIG. 1B shows an exemplary wiring diagram for one embodiment of the blood processing system 100. The compounder pump 102 and the blood pumps 104 are typically powered from a common 12-Volt external power supply 126, and are controlled by an external process controller 120. The process controller 120 includes the user interface 116, a computer 122, and a serial port concentrator 124. The compounder pump 102 and the blood pumps 104 are in communication with the process controller 120 through the serial port concentrator 124, for example, over RS-232 communication links. The blood processing system 100 typically includes a tubing sealer 130 for sealing plastic tubing as necessary for various blood processing operations. The blood processing system 100 typically includes an uninterruptible power supply (UPS) 128 for maintaining electrical power to the 12-Volt power supply, the process controller, and other components in the event of a primary power loss.

Figure 1C:
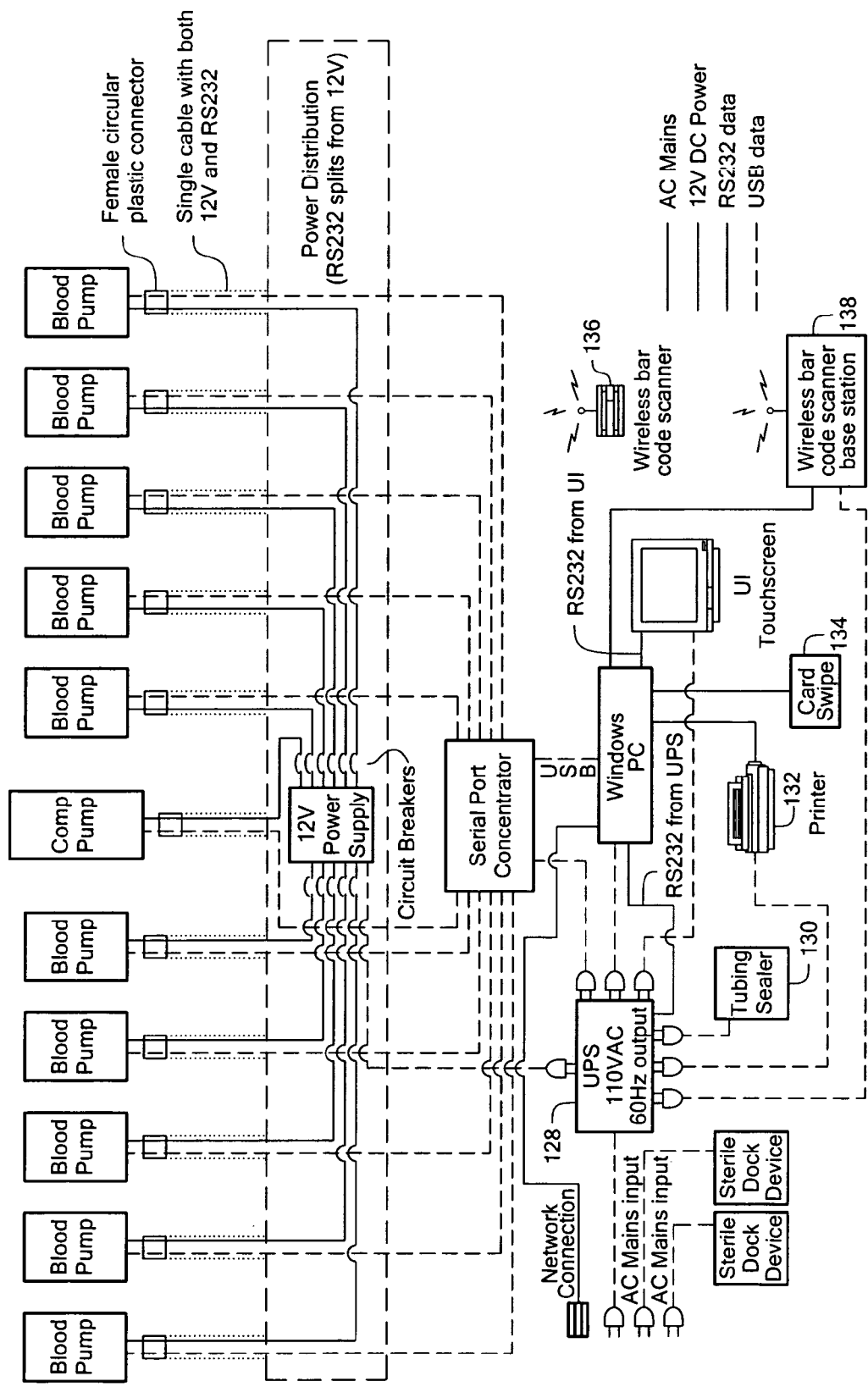
FIG. 1C shows an exemplary wiring diagram for another embodiment of the blood processing system shown in FIG. 1A.

FIG. 1C shows an exemplary wiring diagram for another embodiment of the blood processing system 100. The blood processing system 100 may include a printer in communication with the process controller for printing out reports. The blood processing system 100 may include a card reader 134 in communication with the process controller for card-based operator identification. The blood processing system 100 may include a wireless bar code scanner base station 138 in communication with the process controller for receiving bar code information scanned using a wireless bar code scanner 136. Bar codes are typically used to track the various solution containers and the pumps on which those containers were processed.

The process controller 120 coordinates the actions of the compounder pump 102, the blood pumps 104, and the operator throughout the various mixing operations, as described in greater detail in Application D72. The process controller 120 initiates high level embedded commands within the pumps to move and mix the fluids. The process controller 120 instructs the operator through the setup and teardown of each process through the user interface 116. The user interface 116 is also used to inform the operator of any anomalies that may occur during mixing operations.

When the blood processing system 100 is operating from the uninterruptible power supply 128 and at other appropriate times, the process controller 120 will prevent compounding and other pump operations from starting, although the pumps will generally be allowed to complete any ongoing operations. Furthermore, if the process controller fails, the pumps have internal logic for safely completing or terminating any ongoing operations.

Blood Disposables

In an exemplary embodiment of the present invention, the process controller 120 coordinates blood processing for an entire bank of five blood pumps 104 at a time. Specifically, five pump cassettes, each connected to a RBCC container and an incubation bag for receiving the incubation solution, are loaded respectively into the five blood pumps 104. The five pump cassettes are preferably connected by a single working solution inlet tube to the working solution container so that all five blood pumps draw working solution from the single working solution container. For convenience, the five interconnected pump cassettes along with their respective incubation bags and various plastic tubing may be referred to hereinafter as a "blood disposables set." The blood disposables set is preferably used for a single blood processing cycle and is then discarded. The blood disposables set is described in greater detail in Application D85.

Figure 2:
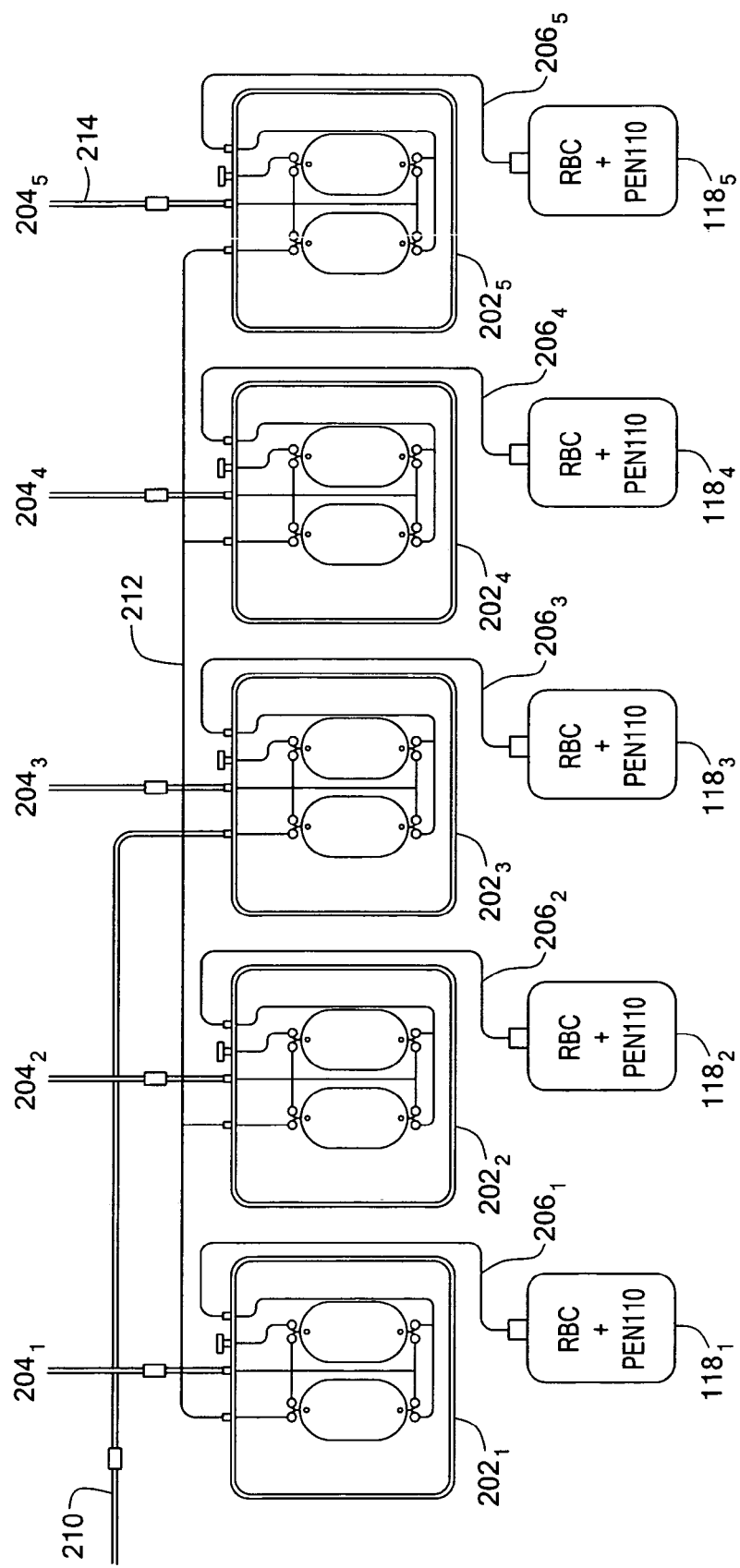
FIG. 2 shows an exemplary blood disposables set in accordance with an embodiment of the present invention.

FIG. 2 shows an exemplary blood disposables set 200 in accordance with an embodiment of the present invention. The blood disposables set 200 includes five pump cassettes $202_{1-5}$, each respectively having a RBCC inlet tube $204_{1-5}$ connected to an RBC inlet port of the pump cassette and an incubation solution outlet tube $206_{1-5}$ connected to an outlet port of the pump cassette and to an incubation-bag $118_{1-5}$. The blood disposables set 200 also includes working solution distribution tubing 212 that connects to a working solution inlet port on each pump cassette $202_{1-5}$ and to a single working solution inlet tube 210 so that the working solution inlet ports of all pump cassettes $202_{1-5}$ are effectively connected to the single working solution inlet tube 210. The working solution inlet tube 210 preferably connects to the working solution distribution tubing 212 close to where the working solution inlet port of the middle pump cassette $202_3$ connects to the tubing 212, and the working solution inlet ports of each concentric pair of pump cassettes is preferably connected to the tubing 212 a substantially equal distance from that center connection such that the working solution inlet ports of the pump cassettes $202_1$ and $202_5$ are essentially equidistant from the center connection and the working solution inlet ports of the pump cassettes $202_2$ and $202_4$ are essentially equidistant from the center connection. Among other things, this spacing of pump cassettes along the tubing 212 facilitates priming of the pumps, as discussed below. In order to perform blood processing, each RBCC inlet tube 204 is connected to a separate RBCC container 106, and the working solution inlet tube 210 is connected to the common working solution container 112. The blood disposables set 200 also includes six break-away closures 214, one on each of the RBCC inlet tubes 204 and one on the working solution inlet tube 210. In order to reduce the likelihood of confusing which RBCC bag and which incubation bag is associated with each pump cassette, the RBCC inlet tubes 204 and the incubation solution outlet tubes 206 are preferably coded, for example, by alternating between color-striped and clear tubing from cassette to cassette.

Figure 3A:
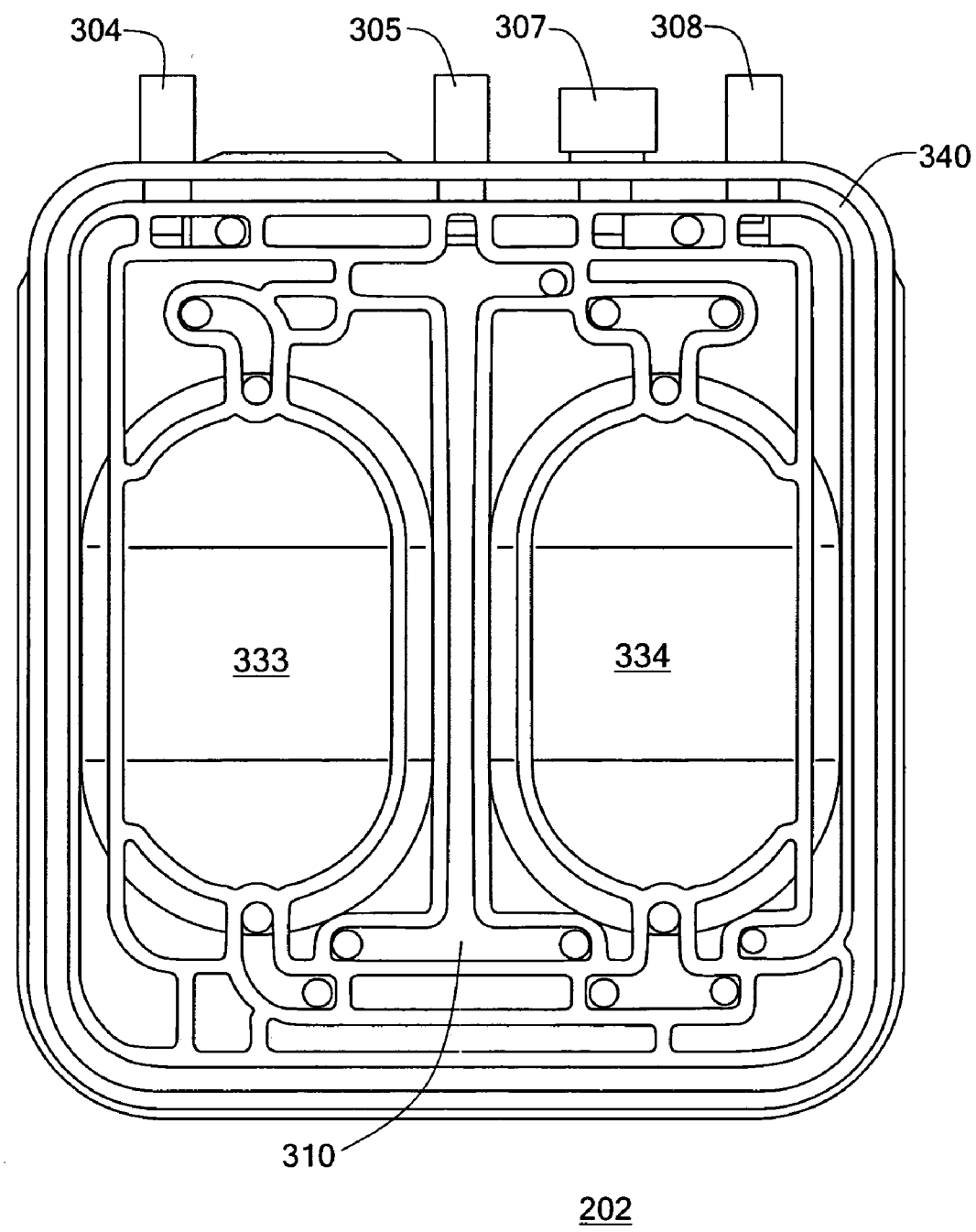
FIG. 3A shows a front view of the pump cassette in accordance with an embodiment of the present invention.

FIG. 3A shows a front view of the pump cassette 202 in accordance with an embodiment of the present invention. The pump cassette 202 is essentially a rigid core including formations and sealing ribs 340 constituting various pumping chambers, fluid valves, and fluid pathways (channels). The rigid core is covered on each side by a flexible membrane (e.g., a flexible PVC sheet). The flexible membranes seal against the core and isolate the blood pump 104 from fluids within the cassette. The pump cassette 202 is designed to interface with the blood pump 104 in only one direction. For example, the pump cassette 202 typically includes an asymmetric feature (such as the placement of tubing) that prevents the blood pump door from closing if the pump cassette 202 is inserted incorrectly.

Among other things, the pump cassette 202 includes a working solution inlet port 304, an RBC inlet port 305, a vent port 307, an outlet port 308 and two pumping chambers, namely a working solution chamber 333 and an RBC chamber 334. During blood processing, working solution from the working solution container 112 is drawn into the working solution chamber 333 through the tubing 210 and 212 and the working solution inlet port 304, and is pumped from the working solution chamber 333 into the channel 310 while RBCC from the RBCC container 106 is drawn into the RBC chamber 334 through the RBCC inlet tube 204, the RBCC inlet port 305, and the channel 310. This causes the working solution and RBCC to be mixed within the channel 310 and the RBC chamber 334. The mixture (incubation solution) is pumped from the RBC chamber 334 to the incubation bag 118 through the outlet port 308 and the incubation solution outlet tube 206.

Figure 3B:
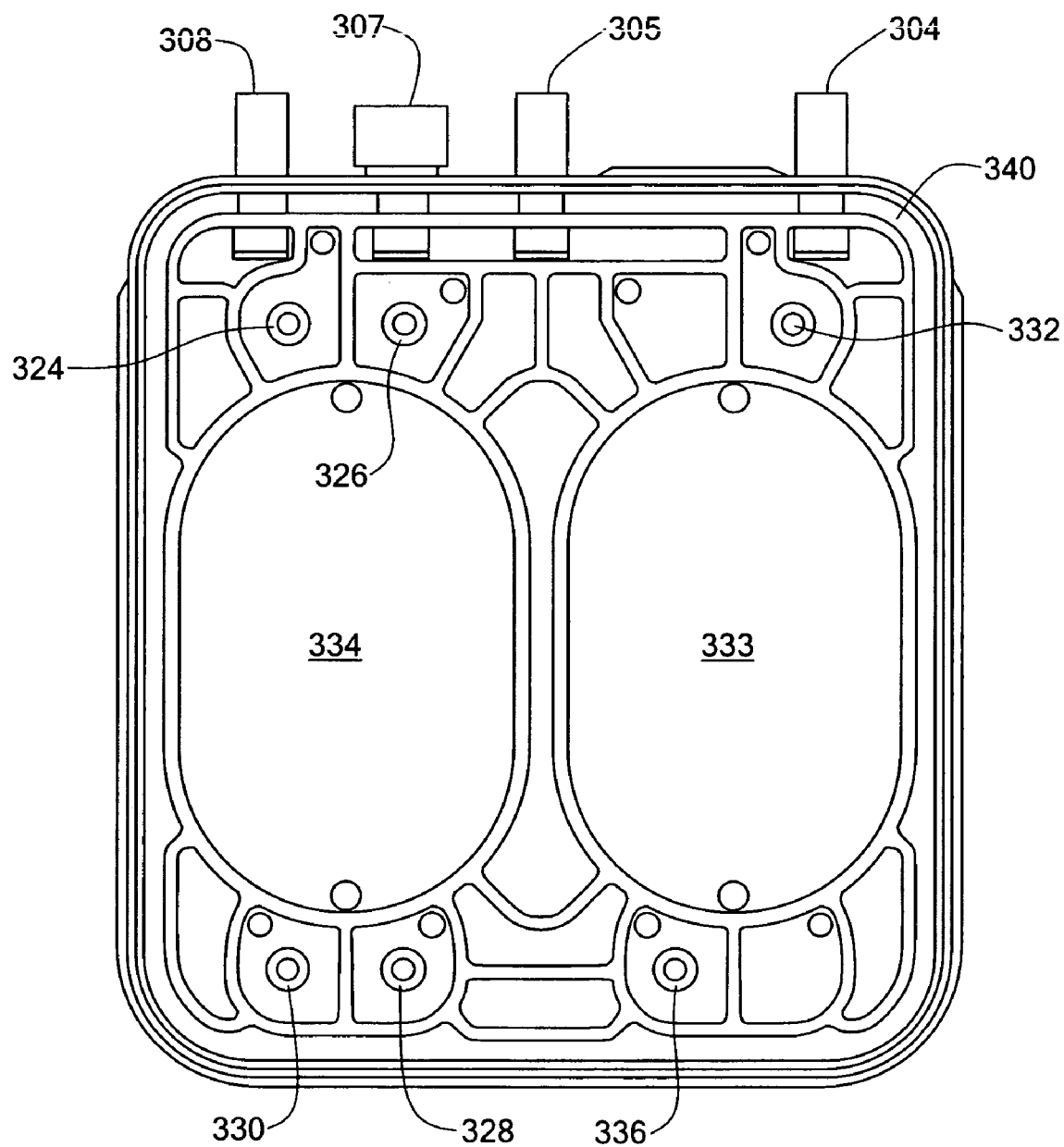
FIG. 3B shows a rear view of the pump cassette in accordance with an embodiment of the present invention.

FIG. 3B shows a rear view of the pump cassette 202 in accordance with an embodiment of the present invention. The rears view of the pump cassette 202 shows various "volcano" valves that are used to open and close various fluid pathways within the pump cassette 202. The valves include an RBC priming valve 326, an RBC valve 328, an incubation bag valve 330, a working solution valve 332, and a working solution connection to RBC line valve 336. The volcano valves and the pumping chambers are all operated pneumatically from the rear of the pump cassette 202, as discussed below.

Blood Pump

As discussed above, each blood pump 104 prepares incubation solution by mixing an anti-pathogen solution with RBCC. A disposable pump cassette 202 is used to handle the various fluids. The pump cassette 202 serves as an interface between the blood pump 104, the RBCC container 106, and the incubation bag 118 so that no working solution, RBCC, or incubation solution comes into actual contact with the components of the blood pump 104. The blood pump 104 preferably uses pneumatics to operate the pump cassette 202 as well as other components, as discussed below.

The blood pump 104 produces the incubation solution by causing working solution to be drawn into the working solution chamber 333 and pumping working solution from the working solution chamber 333 into the channel 310 while drawing RBCC into the RBC chamber 334 through the channel 310. This causes the working solution and RBCC to be mixed within the channel 310 and the RBC chamber 334. The mixture (incubation solution) is pumped from the RBC chamber 334 to the incubation bag 118 through the outlet port 308.

In a typical embodiment of the present invention, the working solution is pumped from the working solution chamber 333 using a pulsing technique in which small quantities of working solution are pumped at predetermined intervals and the pulsing of working solution is adjusted periodically using a closed feedback loop in order to produce an incubation solution having a predetermined concentration of working solution, with predetermined limits. Specifically, the working solution is delivered in a pulsatile mode where the pulse width of the exit valve on the working solution chamber is controlled. The fluid valve is pulsed at a pulse width and interval that is predetermined for each pumping stroke and is adjusted stroke-by-stroke according to the amounts of working solution and RBCC pumped, as described below. The blood pump 104 can support pulse widths above some minimum value, and the interval between pulses is increased in order to achieve an effective pulse width below the minimum value.

The blood pump 104 preferably includes a library of generic pump control (N-Pump) functions. The N-Pump library functions are used to perform various generic pumping operations such as, for example, pumping fluid into a chamber of the pump cassette, pumping fluid out of a chamber of the pump cassette, measuring the mount of fluid pumped, performing air detection, and maintaining tank pressures. The blood pump 104 preferably also includes a Fluid Logic Module (FLM) that contains higher level functions that employ the N-Pump library functions to implement application-specific functions (such as specific logic for mixing the working solution with the RBCC to produce the incubation solution).

The blood pump 104 includes one master board connected to two pump boards that together perform the N-Pump and FLM functions. The master board communicates to each of the pump boards via a multi-drop RS-485 bus. Each pump board controls a single pump chamber of the pump cassette 202 and the valves on its board.

Figure 4:
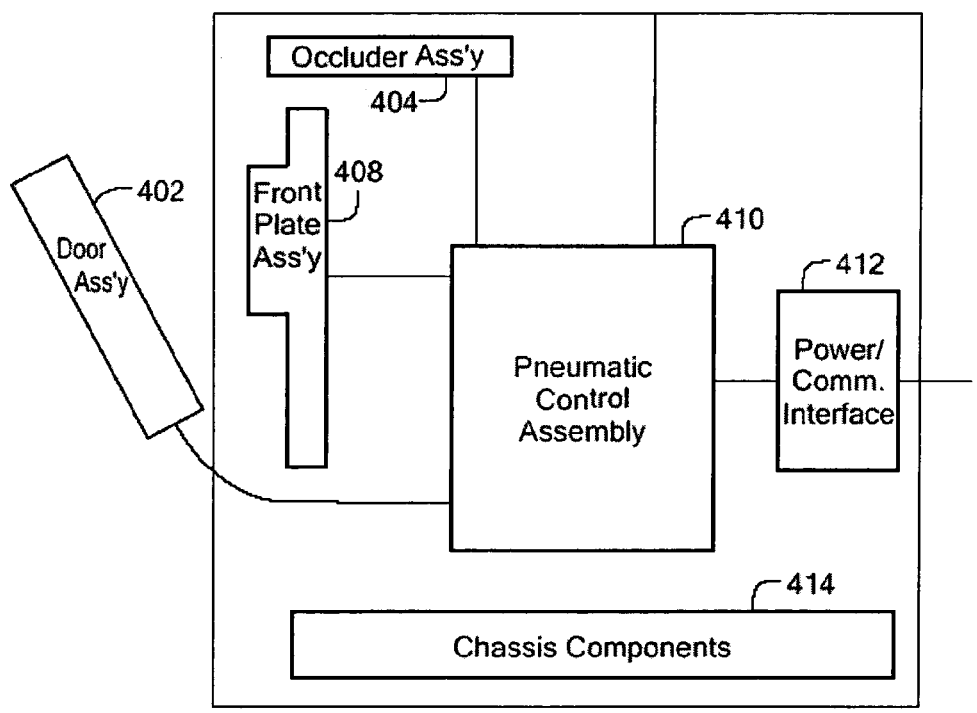
FIG. 4 shows a conceptual block diagram of the blood pump in accordance with an embodiment of the present invention.

FIG. 4 shows a conceptual block diagram of the blood pump 104 in accordance with an embodiment of the present invention. Among other things, the blood pump 104 includes a door assembly 402, an occluder assembly 404, a front plate assembly 408, a pneumatic control assembly 410, a power/communication interface 412 including connectors for the 12-Volt power supply and the RS-232 communication link to the process controller 120, and chassis components 414. Each of these assemblies is discussed below.

Pneumatic Control Assembly

The pneumatic control assembly 410 provides positive and negative air pressure for operating the various other pneumatically controlled components and also acts as the general controller for the blood pump 104. The pneumatic control assembly 410 contains three electromechanical pump module assemblies, namely a tank management module assembly and two chamber module assemblies (one for the working solution pump chamber and one for the RBC pump chamber). Each pump module assembly includes an aluminum manifold, pneumatic valves, pneumatic fittings, a valve interface board, and an electronics board that includes pressure transducers and a dedicated microprocessor. The tank management module assembly handles all communication between the blood pump and the process controller 120, synchronizes pumping of the chamber module assemblies, maintains positive and negative air pressure in various accumulators, seals and unseals the door assembly, engages and disengages the occluders, monitors the door open/closed status, and monitors the air-in-line sensor, as described below. Each chamber management assembly controls a separate one of the pump chambers, and also controls the fluid valves associated with the pump chamber and measures the volume of liquids pumped through the pump chamber.

Figure 5A:
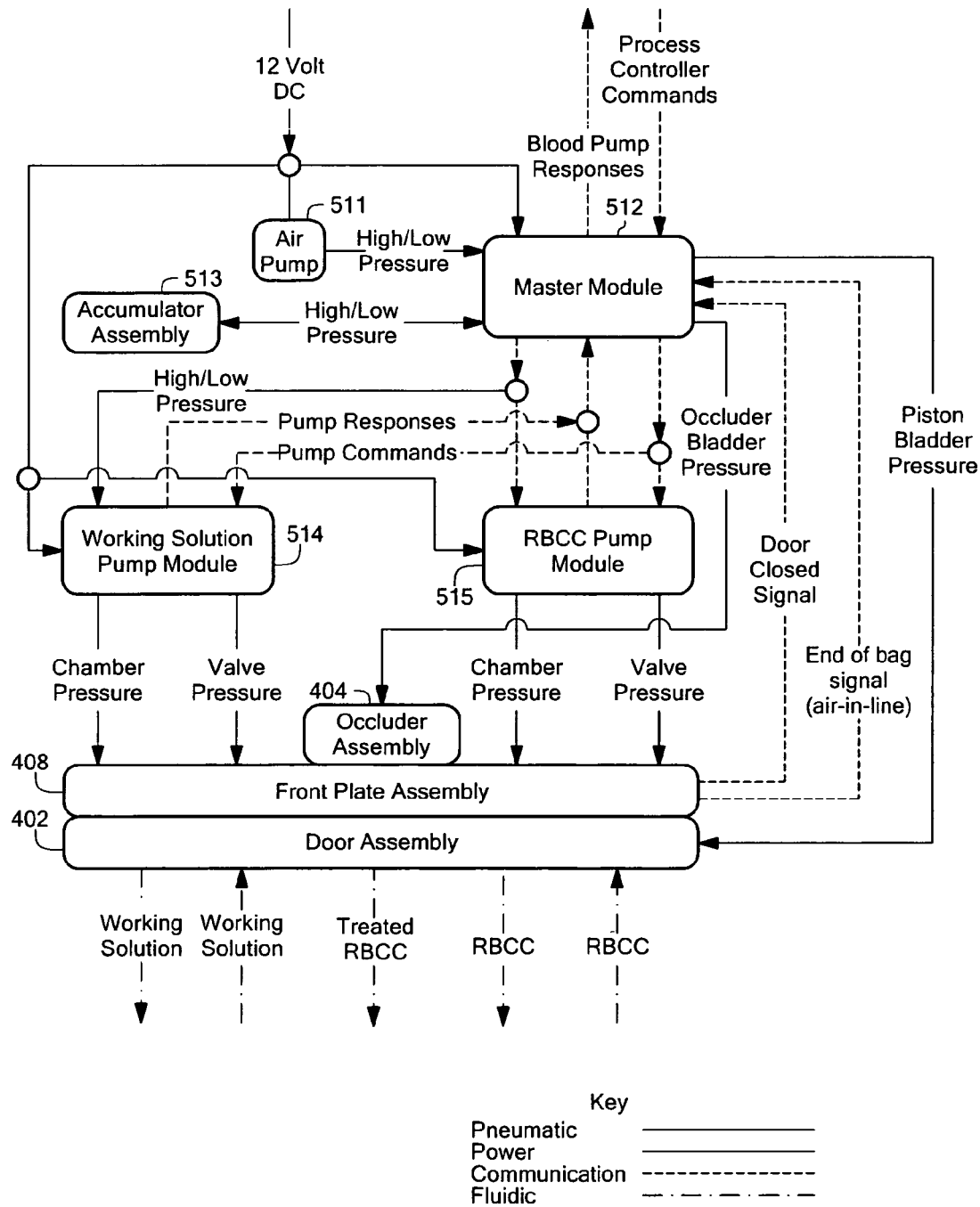
FIG. 5A is an architectural flow diagram showing the relationship between the pneumatic control assembly and the other assemblies in accordance with an embodiment of the present invention.

FIG. 5A is an architectural flow diagram showing the relationship between the pneumatic control assembly 410 and the other assemblies in accordance with an embodiment of the present invention. In this figure, the pneumatic control assembly 410 is represented by master module 512, accumulator assembly 513, working solution pump module 514, and RBCC pump module 515. The air pump 511 is considered to be one of the chassis components 414. The air pump 511 generates high and low air pressure for the master module 512, which stores high and low air pressure in the accumulator assembly 513. The pneumatic control assembly 410 directs air pressure (positive and negative) to the various pneumatic mechanisms of the pump. The master module 512 pneumatically controls bladders in the occluder assembly 404 and a bladder in the door assembly 402, as discussed below. The master module 512 provides high and low air pressure to the working solution pump module 514 and the RBCC pump module 515. The working solution pump module 514 controls the working solution chamber 333 and associated valves of the pump cassette 202 through the front plate assembly 408, and the RBCC pump module 515 controls the RBC chamber 334 and associated valves of the pump cassette 202 through the front plate assembly 408, as described below.

Figure 5C:
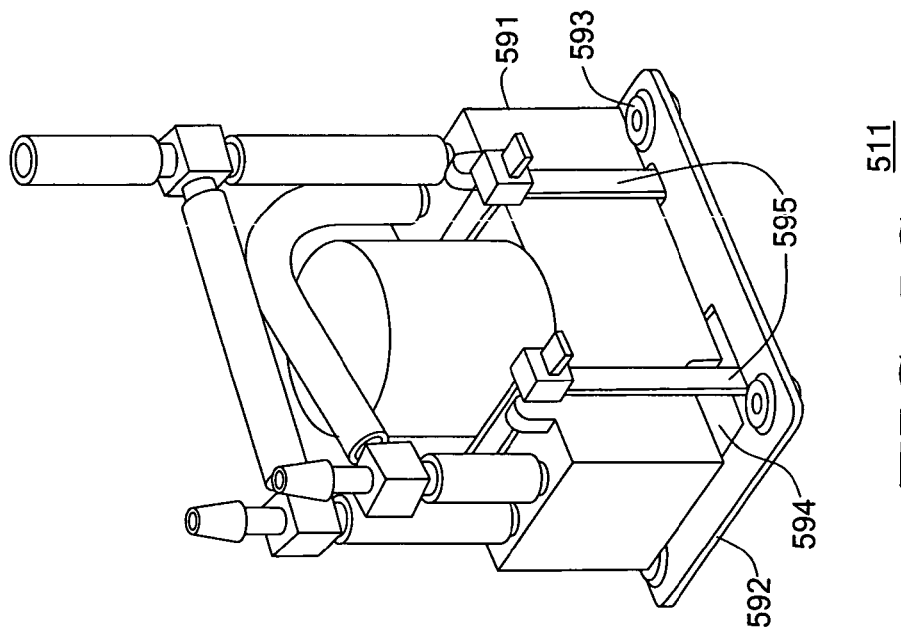
FIG. 5C shows an exemplary embodiment of the air pump in accordance with an embodiment of the present invention.
Figure 5B:
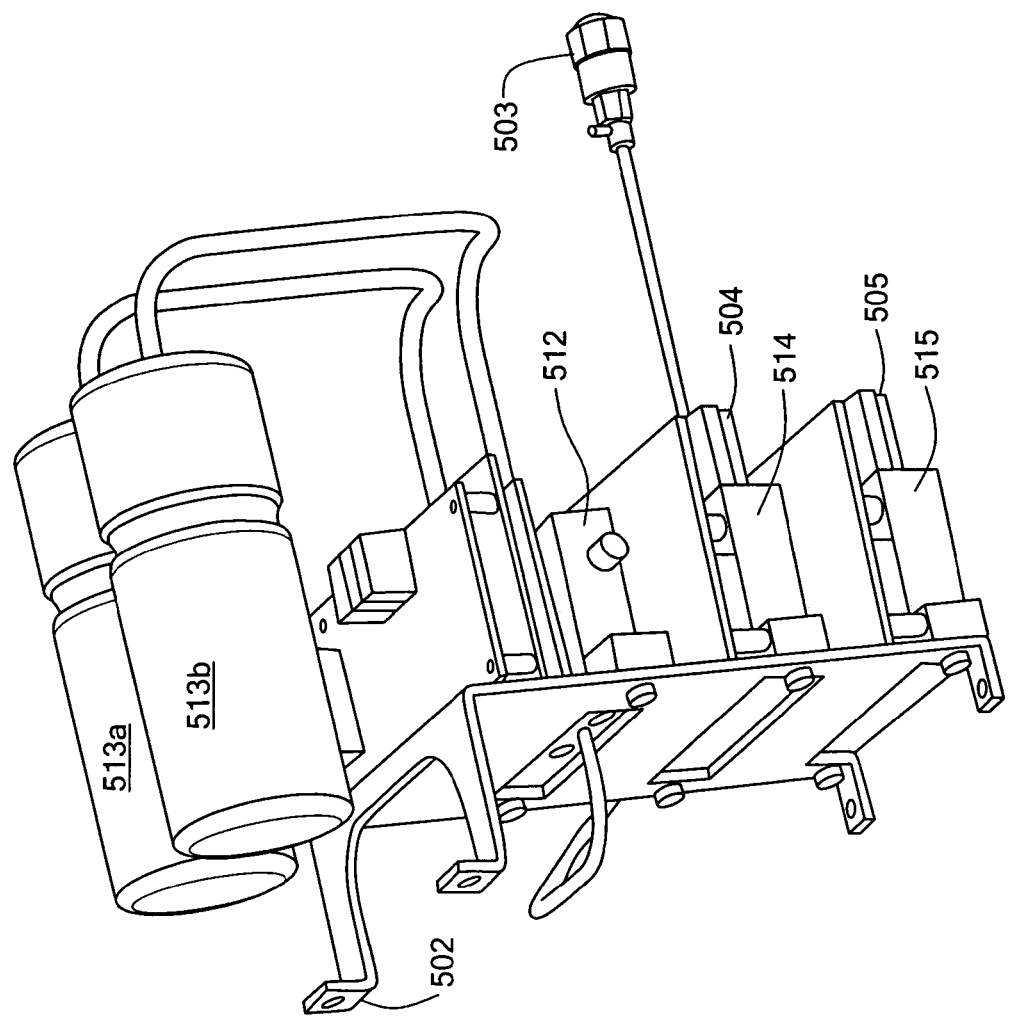
FIG. 5B shows an exemplary embodiment of the pneumatic control assembly in accordance with an embodiment of the present invention.

FIG. 5B shows an exemplary embodiment of the pneumatic control assembly 410 in accordance with an embodiment of the present invention. Among other things, the pneumatic control assembly 410 includes manifold mounting bracket 502, a negative pressure accumulator (pressure bottle) 513a, a positive pressure accumulator (pressure bottle) 513b, a manual door vent mechanism 503, the Tank Management Module Assembly 512, the two Chamber Module Assemblies 514 and 515, and associated tubing and fittings.

The tank management module 512 includes an input/output (I/O) board, a CPU board, a valve-interface board, a pneumatic manifold system, pneumatic valves, pressure transducers 2-vent covers (mufflers), stand-offs, and associated tubing and fittings. The tank management module 512 is used to control the pressures in the accumulators 513, a bladder in the door assembly 402, and bladders in the occluder assembly 404. The I/O board contains electrical controls for controlling LEDs that provide status information to the operator. The pressure transducers are used to monitor the pressures of the accumulators 513 and the bladder in the door assembly 402.

In the un-powered state, the pneumatic valve that controls flow to the bladder in the door assembly 402 preferably shuts closed. This prevents the door from being opened in the event of a loss of power.

In the un-powered state, the pneumatic valves that control flow to the bladders in the occluder assembly 404 are preferably channeled to vent. This causes the occluders to occlude the tubing to prevent further flow of fluid through the tubing, as discussed below.

Each chamber module 514 and 515 includes a CPU board, a valve interface board, pneumatic manifold system, pneumatic valves (including a VSO (variable) valve), a VSX chamber (504 and 505 respectively), O-ring, copper mesh, vent cover (muffler), stand-offs, pressure transducers, and associated tubing and fittings. Each chamber module assembly controls the pneumatics for one of the pumping chambers and its associated valves. The VSX chambers 504 and 505 act as reference volumes in order to measure the volume of fluid that is delivered with the FMS system. The pressure transducers are used to monitor the pressure of the VSX chamber, and of the pumping chamber. The positive pneumatic system contains a pressure relief valve to prevent the air pump from pressurizing the positive system to greater than 16.0 psig.

In the un-powered state, all of the pneumatic valves preferably open the fluid valves to the positive pressure line. This ensures that the fluid valves are closed if there is a loss of power.

The blood pump 104 typically includes three microprocessor systems, one on the tank management module 512 and one on each of the chamber modules 514 and 515. These three microprocessor systems monitor each other for normal operation. Each microprocessor system also monitors key internal processes and data for validity. If any of these monitors fail, a failsafe line permits any of the three processors to stop pumping operations, close all of the fluid valves and occluder, and send an anomaly signal to the process controller. If the blood pump 104 detects an anomaly with the commands received from the process controller (e.g., commands received out of sequence), then the blood pump 104 will stop fluid flow and send an anomaly signal to the process controller.

FIG. 5C shows an exemplary embodiment of the air pump 511 in accordance with an embodiment of the present invention. The air pump 511 includes a pump motor 591 mounted to a pump plate 592 using double-sided tape 594 and two miniature nylon cable ties 595. Four ribbed isolator grommets 593 are inserted into corresponding openings in the pump plate 592.

Front Plate Assembly

The front plate assembly 408 includes all necessary pneumatic pathways to interface to the disposable pump cassette 202. The front plate assembly 408 includes a bezel and a bezel gasket through which the pump cassette 202 is operated. During operation of the blood pump 104, the pump cassette 202 is positioned in the door assembly 402 and is pressed against the front plate assembly 408 in alignment with the bezel and bezel gasket by a bladder in the door assembly 402, as discussed below. Air lines connected to the bezel from the pneumatic control assembly 410 are used to displace membranes of the bezel gasket to operate the various valves and chambers of the pump cassette 202.

Figure 6A:
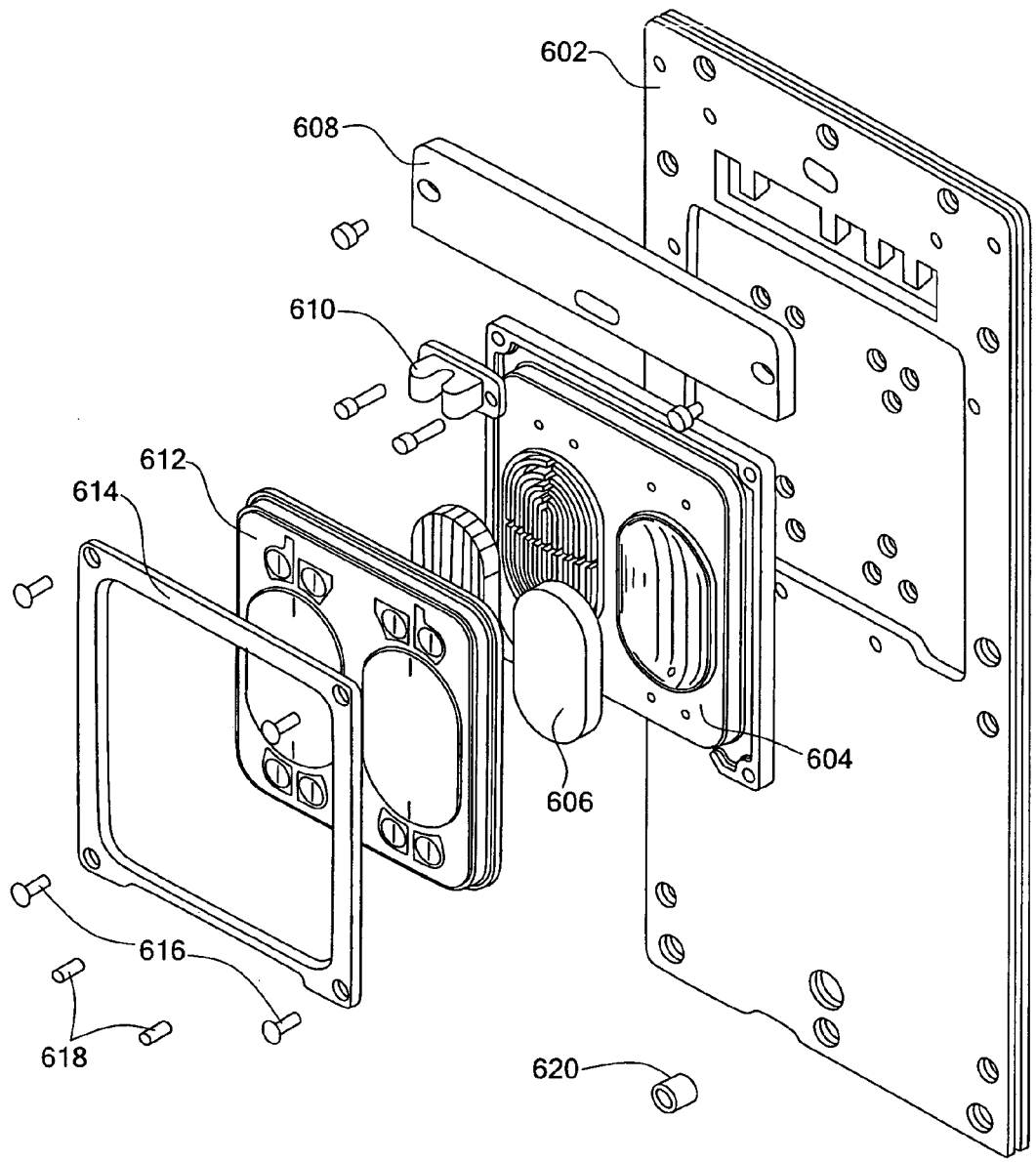
FIG. 6A shows an exploded view of an exemplary front plate assembly in accordance with an embodiment of the present invention.

FIG. 6A shows an exploded view of an exemplary front plate assembly 408 in accordance with an embodiment of the present invention. Among other things, the front plate assembly 408 includes a rigid front plate 602 to which are mounted a bezel 604, chamber foam 606, spacer 608, air-in-line sensor 610, bezel gasket 612, gasket retainer 614, hardware 616, dowel pins 618, and grommet 620. The bezel 604, chamber foam 606, and bezel gasket 612 are mounted to the front plate 602 by the gasket retainer 614 and associated hardware 616, forming a bezel assembly. This bezel assembly is used to control pumping and mixing of fluids using the pump cassette 202, as described below. The front plate 602 includes holes for allowing air tubes to pass between the rear of the bezel 604 and the pneumatic control assembly 410, which is typically situated behind the front plate 602. The front plate 602 also includes openings for occluder blades and for engaging a door latch mechanism, as described below. The air-in-line sensor 610 is positioned so as to align with and engage the RBCC inlet tube 204, and is used during blood processing to detect air in the RBCC inlet tube 204 indicating that there is no more RBCC to be processed.

Figure 6B:
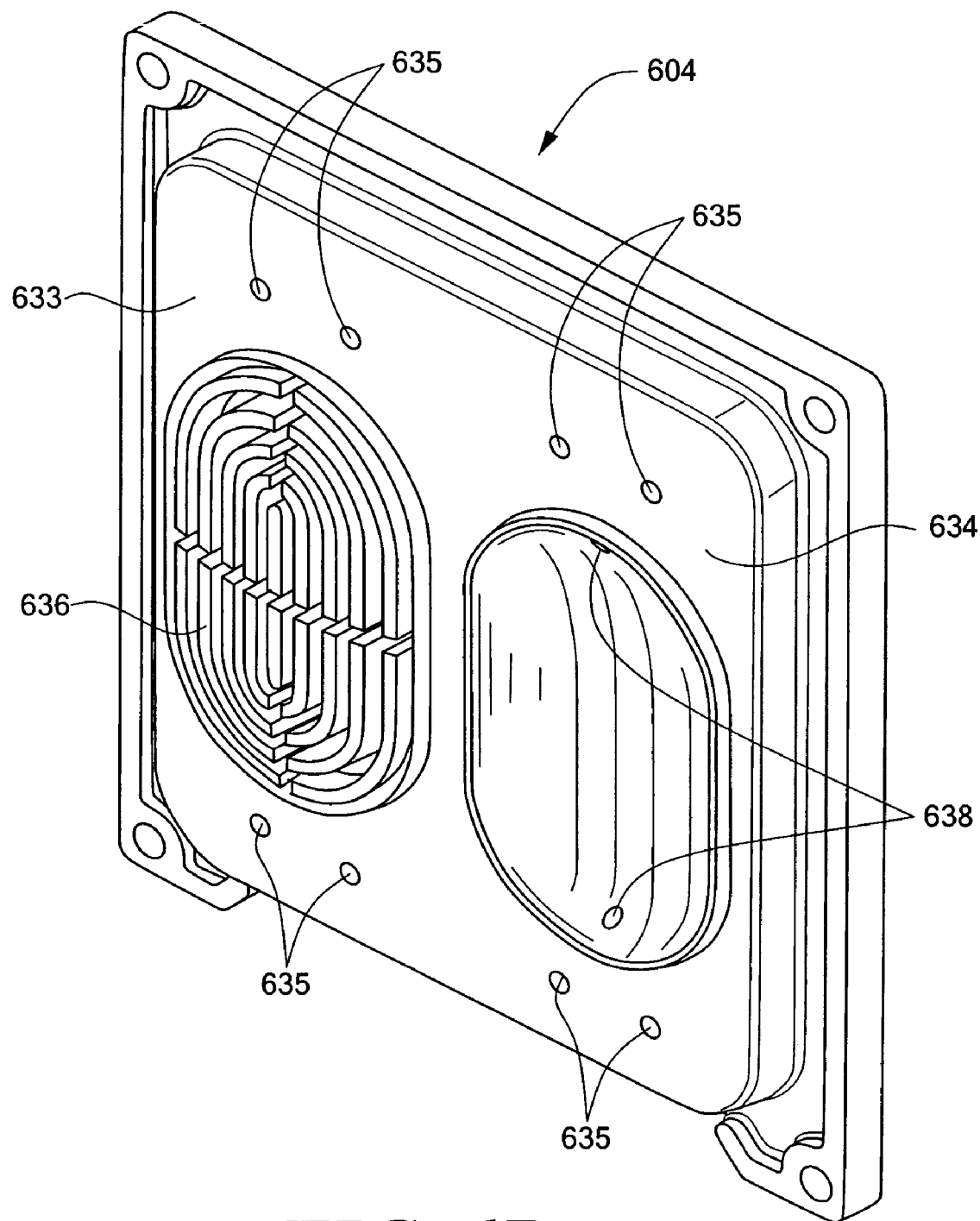
FIG. 6B shows a front view of an exemplary bezel in accordance with an embodiment of the present invention.

FIG. 6B shows a front view of an exemplary bezel 604 in accordance with an embodiment of the present invention. The bezel 604 is preferably a molded polycarbonate/ABS unit including, among other things, a working solution chamber cavity 633 for operating the working solution chamber 333 of the pump cassette 202, an RBC chamber cavity 634 for operating the RBC chamber 334 of the pump cassette 202, and various valve cavities 635 for operating the various valves of the pump cassette 202. Each of the chamber cavities 633 and 634 typically includes two air holes 638 through which air is pumped into and out of the chamber cavity. The working solution chamber cavity 633 is preferably molded with rib structures 636 that allow for airflow within the working solution chamber cavity 633 but mechanically restrict the amount of working solution that can be drawn into the working solution chamber 333 of the pump cassette 202. The bezel with rib structures is described in greater detail in Application D75. The compounder 102 preferably uses the same molded bezel 604 as the blood pump 104, but with the rib structures 636 removed (e.g., by precision machining) to allow for greater pumping capacity.

Figure 6C:
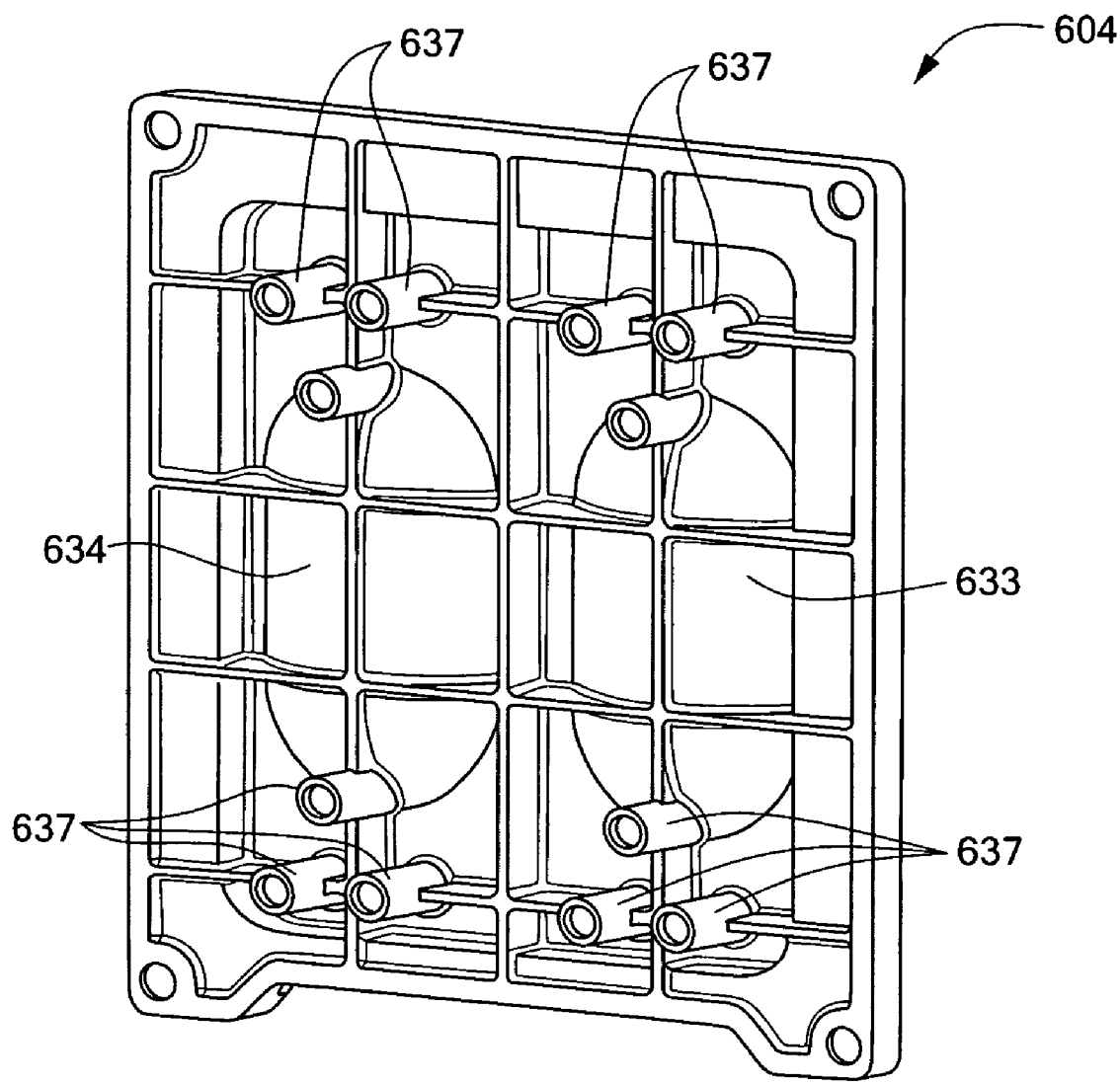
FIG. 6C shows a rear view of an exemplary bezel in accordance with an embodiment of the present invention.

FIG. 6C shows a rear view of the bezel 604 in accordance with an embodiment of the present invention. The bezel 604 includes integral solvent bondable tubing connections (ports) 637 to which pneumatic tubing from the pneumatic control assembly 410 are connected. In this embodiment, each of the valve cavities 635 is associated with a single integral port 637, and each of the chamber cavities 633 and 634 are associated with two integral ports 637. The integral ports 637 allow the pneumatic connections to be made without independent fittings and accompanying O-rings.

Figure 6E:
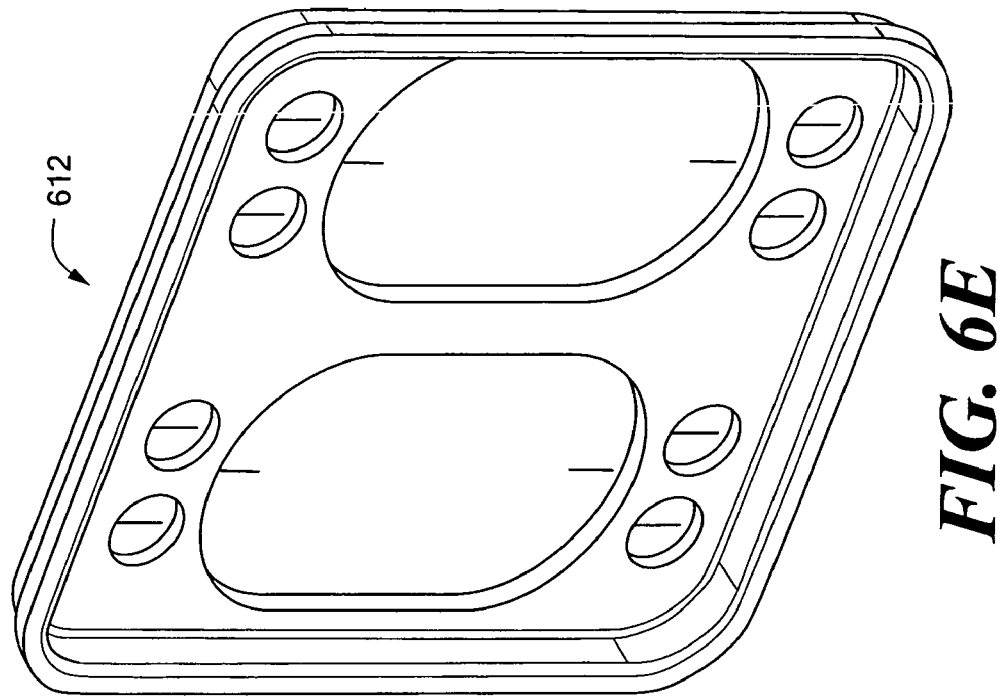
FIG. 6E shows a rear view of an exemplary bezel gasket in accordance with an embodiment of the present invention.
Figure 6D:
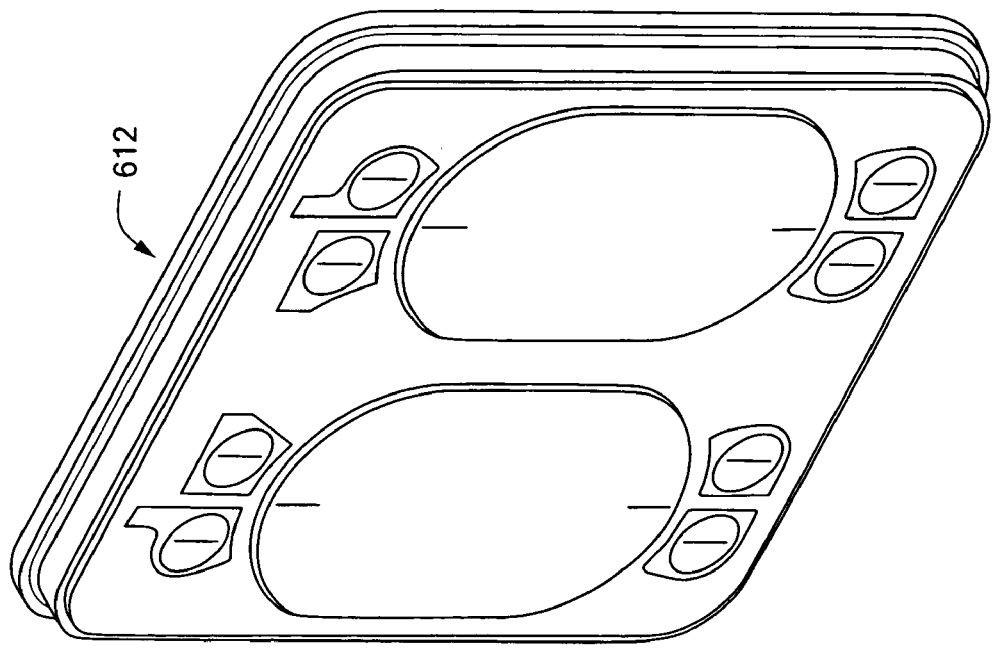
FIG. 6D shows a front view of an exemplary bezel gasket in accordance with an embodiment of the present invention.

FIG. 6D shows a front view of an exemplary bezel gasket 612 in accordance with an embodiment of the present invention. The bezel gasket 612 fits over the front of the bezel 604 and acts as an interface between the bezel 604 and the pump cassette 202 for sealing the fluid paths of the pump cassette 202 and for actuating the chambers and valves of the pump cassette 202. The pump cassette 202 is pressed firmly against the front side of the bezel gasket 612 during blood processing in order to produce an air-tight seal between the bezel gasket 612 and the pump cassette 202. The bezel gasket 612 includes membranes that correspond to the chamber cavities and valve cavities. Positive and negative air pressure produced through the bezel cavities operate on the bezel gasket membranes, which in turn operate on the chambers and valves of the pump cassette 202.

FIG. 6E shows a rear view of an exemplary bezel gasket 612 in accordance with an embodiment of the present invention. The rear side of the bezel gasket 612 contacts the front side of the bezel 604, and is pressed firmly against the bezel 604 during blood processing in order to produce an air-tight seal. The bezel gasket 612 includes membranes that correspond to the chamber cavities and valve cavities. Positive and negative air pressure produced through the bezel cavities operate on the bezel gasket membranes, which in turn operate on the chambers and valves of the pump cassette 202.

Door Assembly

The door assembly 402 mounts to the front plate assembly 408, and provides a means to load and align the disposable pump cassette 202 within the blood pump 104. The door assembly 402 provides a force on the pump cassette 202 against the bezel assembly of the front plate assembly 408 in order to provide sealing of the cassette's fluid paths and valves, as described in greater detail in Application D73. The door assembly 402 includes a special latch system that helps maintain the seal, and also helps prevent accidental opening of the door during blood processing, as described in greater detail in Application D74. The door assembly 402 also provides a surface for the occluders to function against, as described below.

Figure 7A:
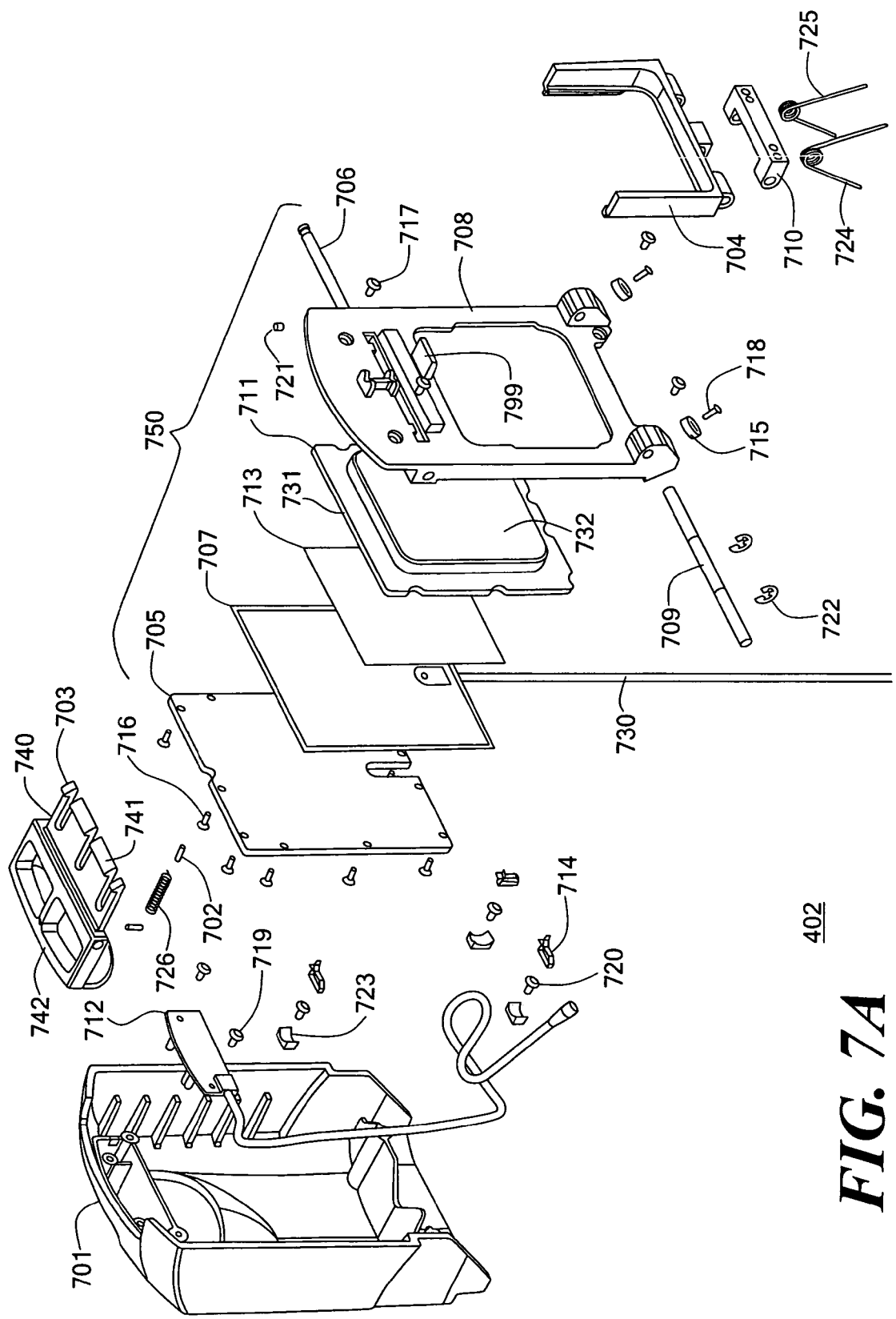
FIG. 7A shows an exploded view of the door assembly in accordance with an embodiment of the present invention.

FIG. 7A shows an exploded view of the door assembly 402 in accordance with an embodiment of the present invention. Among other things, the door assembly 402 includes a door cowl 701, a latch spring post 702, a door latch 703, a cassette receptacle 704, a back plate 705, a latch pin 706, a bladder 707 with an attached pneumatic circuit 730, a frame 708, a door pin 709, a door mounting bracket 710, a piston assembly 711 including a piston plate 731 and a piston cover 732, a human interface board assembly 712, double coated tape 713, a miniature cable tie 714, recessed bumpers 715, E-rings 722, cable tie mount 723, torsion springs 724 and 725, extension spring 726, a cassette orientation tab 799, and various screws 716, 717, 718, 719, 720, and 721. The human interface board assembly 712 is mounted to the inside of the door cowl 701. The piston assembly 711 includes a rigid plate 731 having a protrusion that is covered by the piston cover 732. The bladder 707, double coated tape 713, and piston assembly 711 are sandwiched between the back plate 705 and the frame 708, which are mechanically coupled together to form a frame assembly 750. The door latch 703 is positioned so that a handle portion is accessible from a front side of the door cowl 701. The frame assembly 750 is mounted to the inside of the door cowl 701 so that a latch portion of the door latch 703 protrudes through the frame assembly 750 and the frame assembly 750 holds the door latch 703 in place. The cassette receptacle 704 is pivotally mounted to the frame 708 using the door mounting bracket 710, the door pin 709, and the E-rings 722. Recessed bumpers 715 reduce strain on the door if the door is opened too far or with excessive force. The torsion springs 724 and 725 aid the operator in closing the door, as the door has considerable weight due to the many components.

The cassette orientation tab 799 prevents the door from being closed if the pump cassette is oriented incorrectly in the cassette receptacle 704.

The bladder 707 is coupled to, and controlled by, a pneumatic circuit 730 that provides positive and/or negative air pressure to the bladder 707. Positive pressure supplied to the bladder 707 causes the bladder 707 to expand in the direction of the frame 708. This, in turn, causes the entire piston assembly 711 to move toward the control assembly 408, such that the piston cover 732 presses against the pump cassette 202 and/or cassette receptacle 704, thereby producing an outward force on the door 402 away from the control assembly 408. Alternatively, supplying negative pressure to the bladder 707 causes the piston assembly 711 to move away from the pump cassette 202 and/or cassette receptacle 704, thereby reducing the outward force on the door 402 away from the control assembly 408.

The door assembly is designed to permit single-handed operation, specifically by pulling up on the handle. However, the door latch 703 is designed so that the door cannot be easily opened when the pump cassette is in place in the cassette receptacle 704 with the door closed and the bladder 707 is inflated. Specifically, the latch portions of the door latch 703 have undercuts that are engaged by recesses in the front plate assembly 408. When the pump cassette is in place in the cassette receptacle 704 with the door closed and the bladder 707 is inflated so as to push the pump cassette against the bezel components of the front plate assembly 408, a sufficient force is generated between the door assembly 402 and the front plate assembly 408 to prevent the door handle from being easily lifted. This door locking mechanism is described in greater detail in Application D74.

Figure 7B:
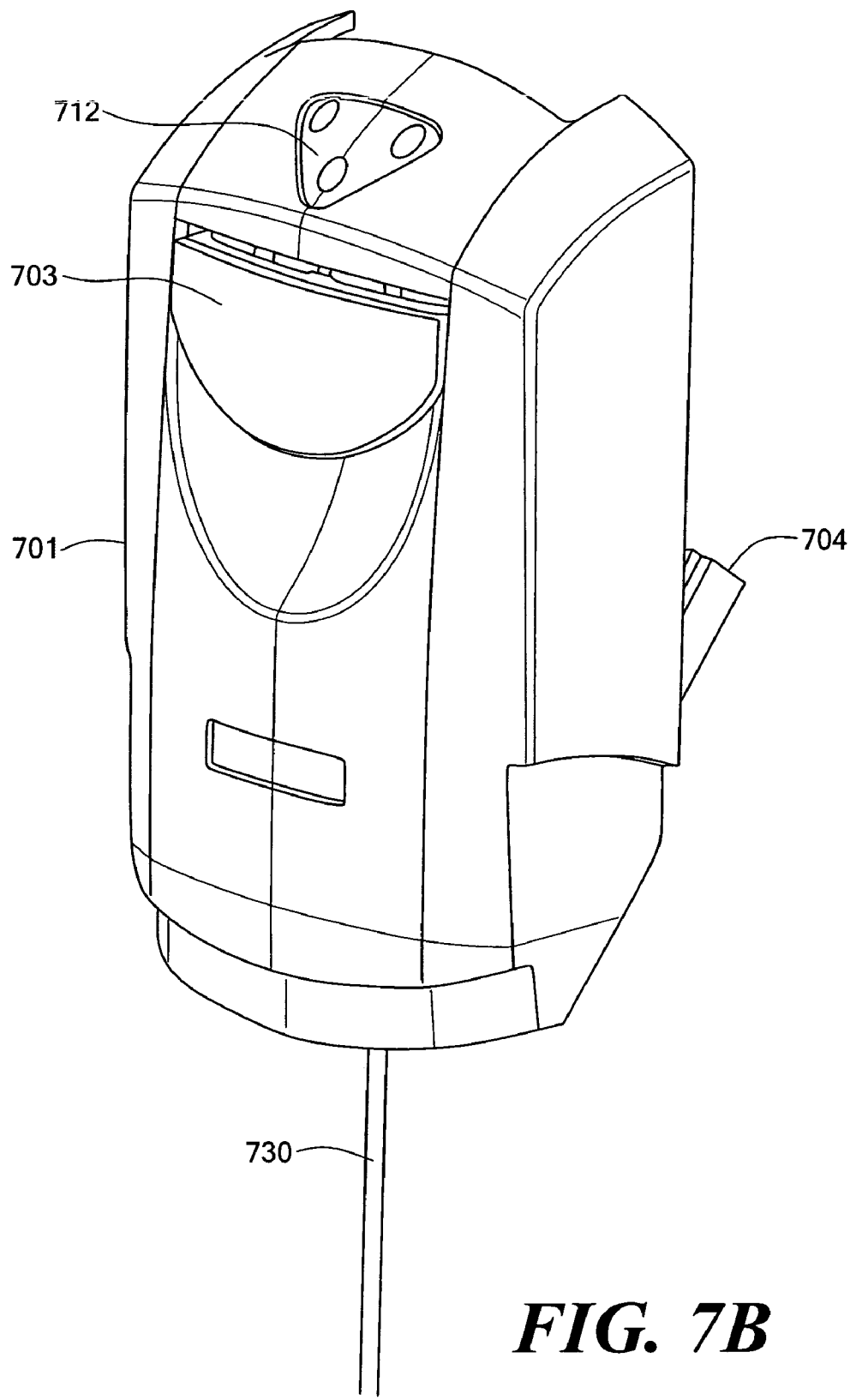
FIG. 7B shows a front perspective view of the door assembly in accordance with an embodiment of the present invention.

FIG. 7B shows a front perspective view of the door assembly 402 in accordance with an embodiment of the present invention. The human interface board assembly 712 having LEDs and the handle portion of the door latch 703 are visible from the front of the door cowl 701. A portion of the cassette receptacle 704 and a portion of the pneumatic circuit 730 are also visible.

Figure 7C:
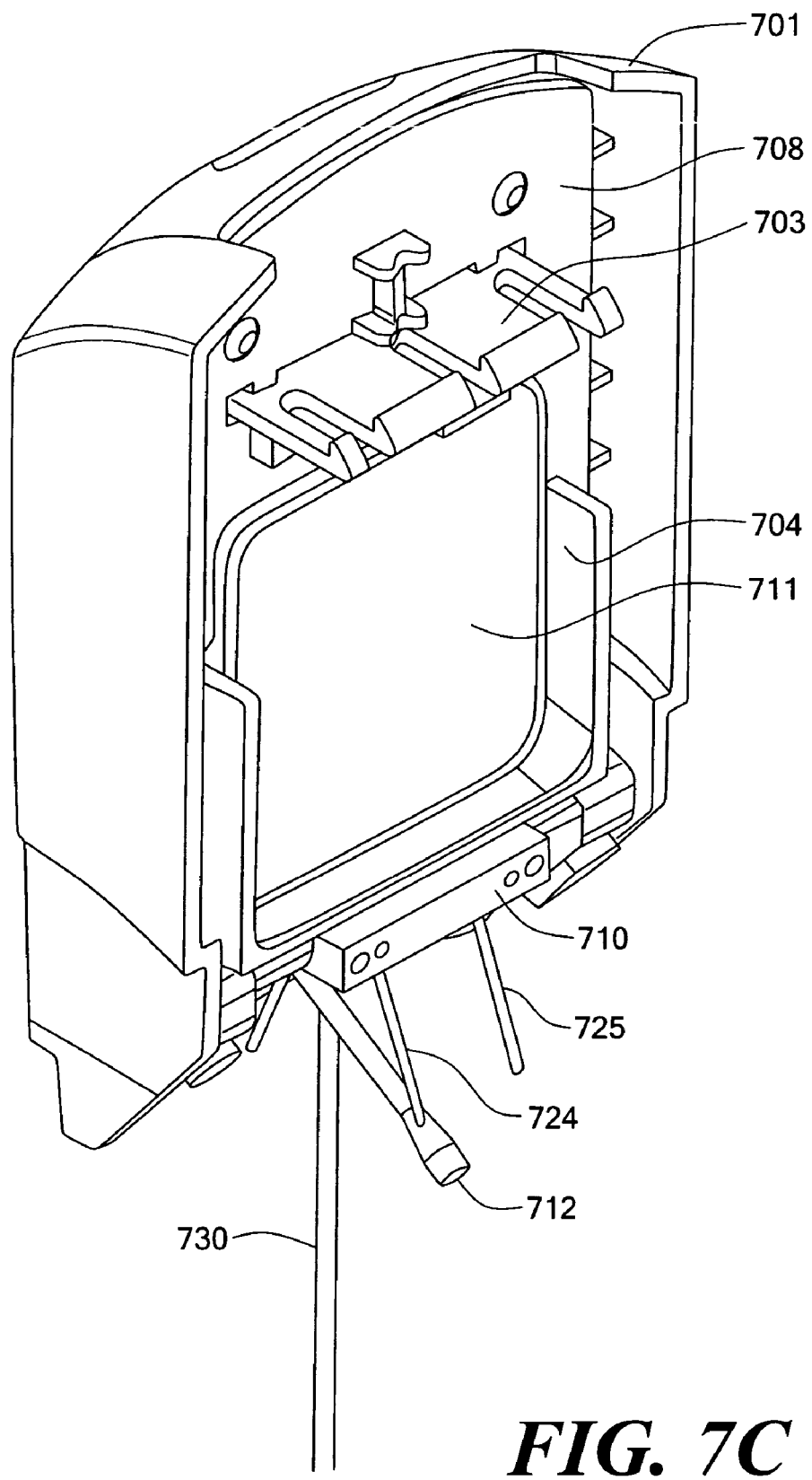
FIG. 7C shows a rear perspective view of the door assembly in accordance with an embodiment of the present invention, in which the cassette receptacle is in a retracted position.

FIG. 7C shows a rear perspective view of the door assembly 402 in accordance with an embodiment of the present invention, in which the cassette receptacle 704 is in a retracted position. Visible at the rear of the door cowl 701 are the frame 708, the latch portion of the door latch 703, the cassette receptacle 704, the piston assembly 711, the door mounting bracket 710, the torsion springs 724 and 725, a portion of the human interface board assembly 712, and a portion of the pneumatic circuit 730.

Figure 7D:
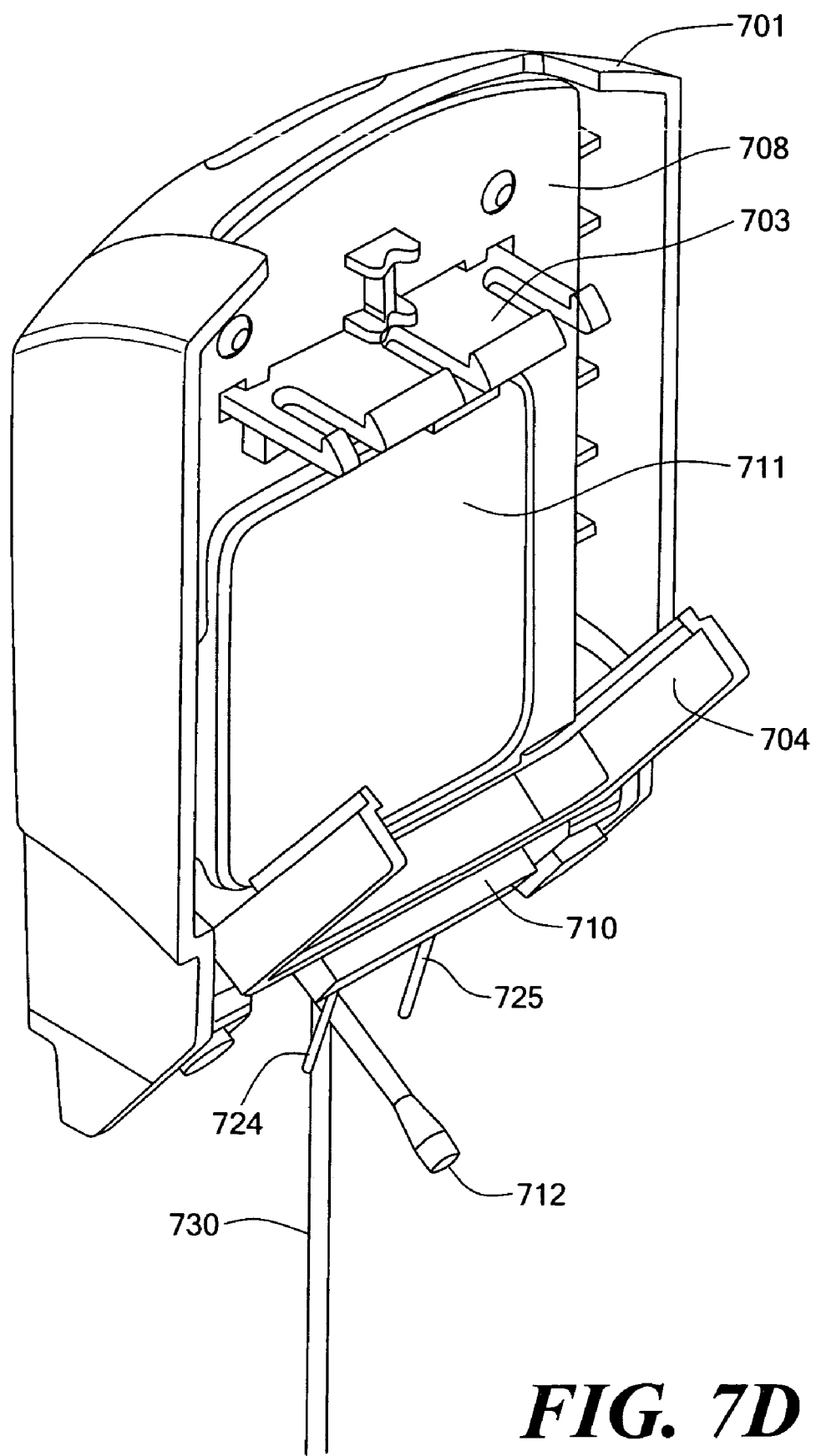
FIG. 7D shows a rear perspective view of the door assembly in accordance with an embodiment of the present invention, in which the cassette receptacle is in an open position.

FIG. 7D shows a rear perspective view of the door assembly 402 in accordance with an embodiment of the present invention, in which the cassette receptacle 704 is in an open position. Visible at the rear of the door cowl 701 are the frame 708, the latch portion of the door latch 703, the cassette receptacle 704, the piston assembly 711, the door mounting bracket 710, the torsion springs 724 and 725, a portion of the human interface board assembly 712, and a portion of the pneumatic circuit 730.

Occluder Assembly

The occluder assembly 404 mounts to the back of the front plate assembly 408, and is used to selectively occlude the RBCC inlet tube 204, the incubation solution outlet tube 206, and the working solution distribution tube 212 as needed for testing, blood processing, and protection in the event of a failure. In the blood pump 104, the occluder assembly 404 includes two occluders, one operating on both the RBCC inlet tube 204 and the incubation solution outlet tube 206, and the other operating on the working solution distribution tube 212. The occluders are controlled pneumatically, and can be controlled independently.

In a typical embodiment of the present invention, each occluder includes an occluder blade that is operated by a flat spring and an inflatable bladder. The occluder blade is coupled to one end of the spring. When the bladder is deflated, the spring extends the occluder blade into an occluding position, which blocks the passage of fluid through the tube(s). When the bladder is inflated, the bladder bends the spring so as to retract the occluder blade from the occluding position, which enables the passage of fluid through the tube(s). In the event of a loss of pneumatics, the occluder defaults to the occluded position so as to prevent fluid from passing through the tubing.

Figure 8:
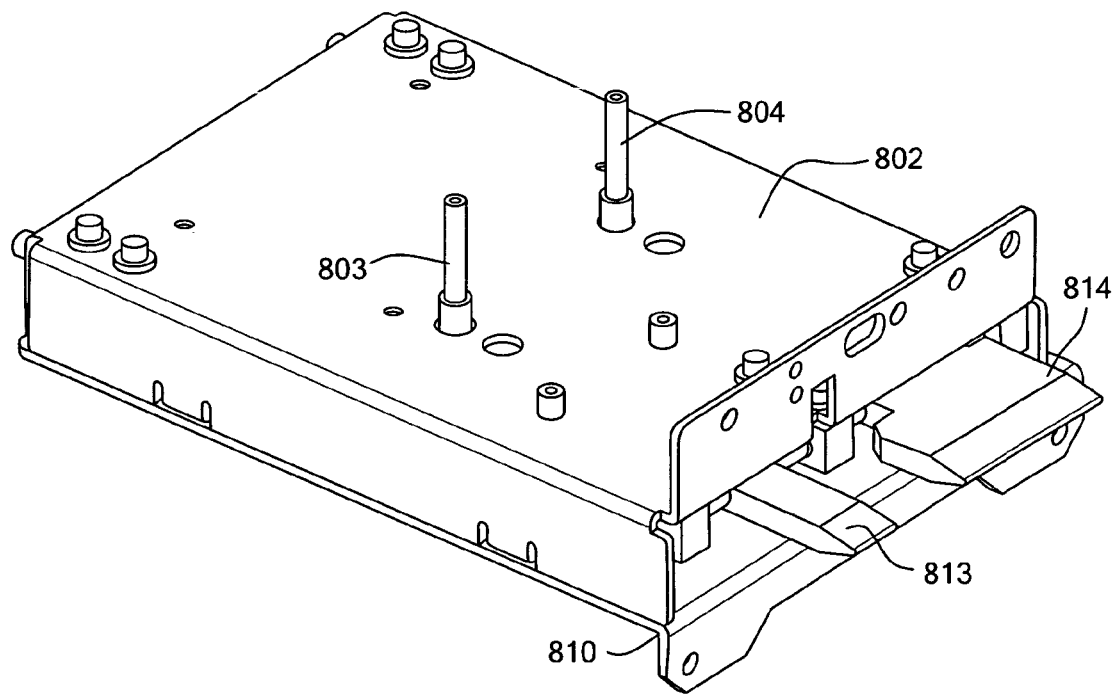
FIG. 8 shows a side perspective view of the occluder assembly in accordance with an embodiment of the present invention.

FIG. 8 shows a side perspective view of the occluder assembly 404 in accordance with an embodiment of the present invention. The occluder assembly 404 includes, among other things, a bottom housing 801, a top housing 802, a first occluder having an occluder blade 813 and other components operated pneumatically through tube 803, and a second occluder having an occluder blade 814 and other components operated pneumatically through tube 804. The occluder assembly 404 is mounted to the front plate assembly 408, with the occluder blades 813 and 814 protruding through slots in the front plate assembly 804. The tubes 803 and 804 are connected to the pneumatic control assembly 410.

Figure 9:
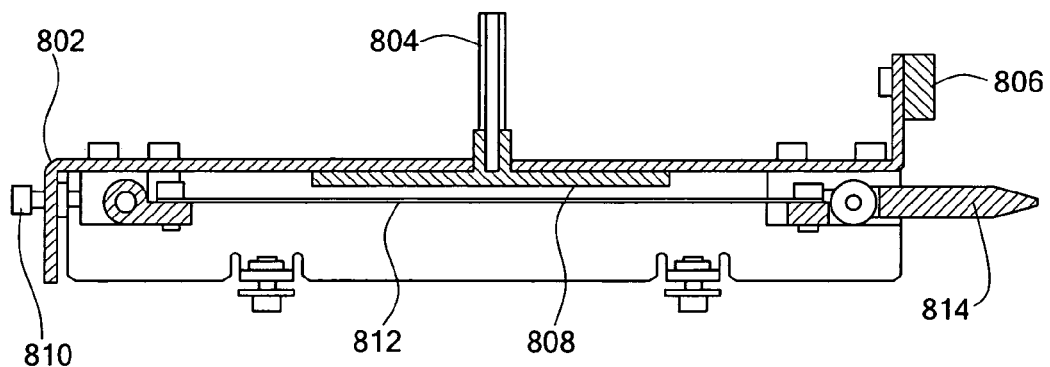
FIG. 9 shows a cross-sectional view of an occluder in accordance with an embodiment of the present invention.

FIG. 9 shows a cross-sectional view of an occluder in accordance with an embodiment of the present invention. Among other things, the occluder includes a flat occluder spring 812 having a rear end coupled to the top housing 802 and a front end coupled to the occluder blade 814, a bladder 808 situated between the top housing 802 and the spring 812, the tube 804 coupled to the bladder 808, and an adjuster 810 for adjusting the protrusion of the occluder blade 814. When the bladder 808 is inflated, the occluder spring 812 is deflected downward at the middle so as to shorten the effective length of the occluder spring 812 and retract the occluder blade 814. When the bladder 808 is deflated, the occluder spring 812 extends flat and therefore extends the occluder blade 814. The occluder blade 814 moves within guides (not shown) that allow the spring to extend and retract the occluder blade 814.

Figure 10:
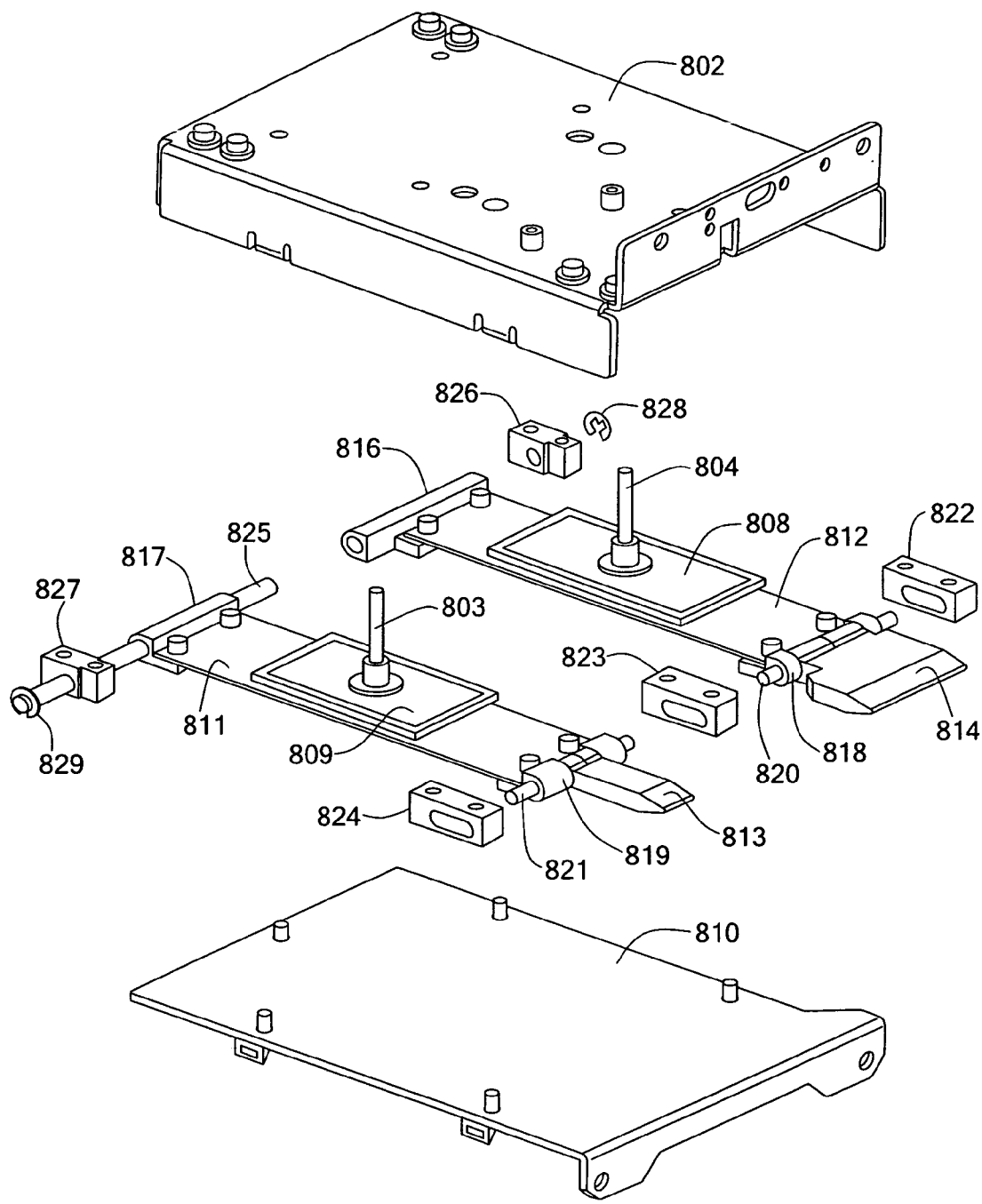
FIG. 10 shows an exploded view of the occluder assembly in accordance with an embodiment of the present invention.

FIG. 10 shows an exploded view of the occluder assembly 404 in accordance with an embodiment of the present invention. Among other things, the occluder assembly 404 includes enclosure top 802, enclosure bottom 810, a first occluder including an occluder blade 813, a shaft 821, a front bracket 819, a rear bracket 817, a bladder 809, and a tube 803, and a second occluder including an occluder blade 814, a shaft 820, a front bracket 818, a rear bracket 816, a bladder 808, and a tube 804. The occluder blade 813 mounts to the front bracket 819 via the shaft 821, while the occluder blade 814 mounts to the front bracket 818 via the shaft 820. The rear brackets 816 and 817 are mounted to the enclosure top 802 via shaft 825, blocks 826 and 827, and clamps 828 and 829. The rear brackets 816 and 817 are held in a substantially fixed position, although the rear brackets 816 and 817 are able to rotate about the shaft 825 as needed for operation of the occluders. The front bracket 819 is mounted to the enclosure top 802 via shaft 821 and sliding blocks 823 and 824, while the front bracket 818 is mounted to the enclosure top 802 via shaft 820 and sliding blocks 822 and 823. The front brackets 818 and 819 are able to slide forward and backward along channels formed in the sliding blocks 822, 823, and 824 as needed for operation of the occluders. Thus, the blocks 826 and 827 constrain the position of the occluder blades and act as bearing surfaces as the rear shaft rotates, and the sliding blocks 822, 823, and 824 act as bearing surfaces for the front shafts as the occluder blades are actuated and released. It should be noted that the present invention is not limited to the block-type bearings shown, but rather various types of bushings, bearings, fixed blocks, moving blocks, or any combination thereof could be used to permit rotation of the rear shafts and/or brackets and translational movement of the front shafts. The occluder blades 813 and 814 can be manually retracted if necessary. The edge of the occluder blades 813 and 814 that engages the tubing are typically rounded so as not to cut or crease the tubing.

Chassis Components

The chassis components 414 include various mechanical hardware components that are not considered part of the other assemblies. Among other things, the chassis components 414 include the DC air pump 511, a chassis base, a door sensor (and cable), mounting foot grommets, skins (housing), and associated hardware and fasteners. The housing includes a mounting point, on the back of the unit, for the manual piston bladder (door) vent 503.

Pump Cassette Handling

Figure 11:
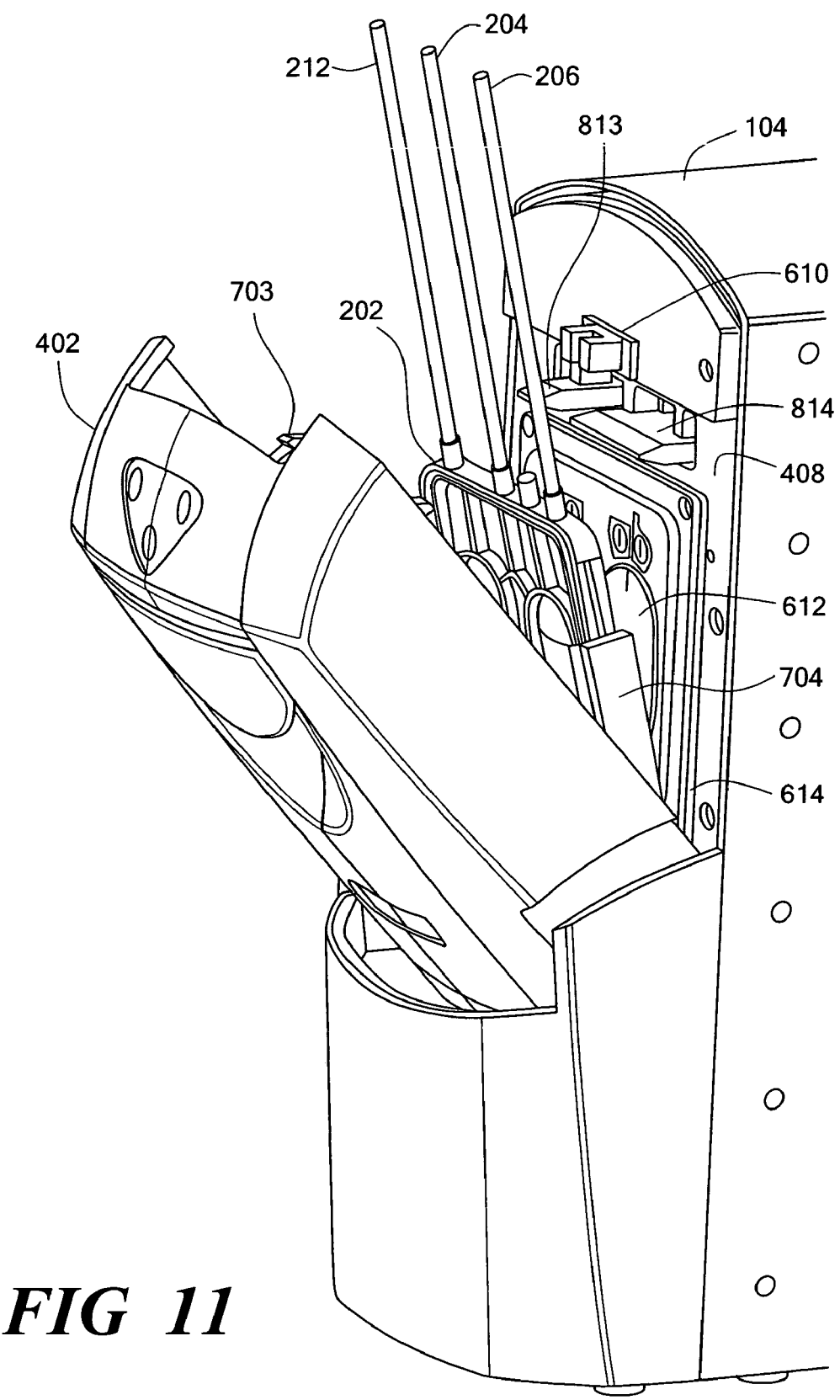
FIG. 11 is a schematic diagram showing the pump cassette installed in the blood pump in accordance with an embodiment of the present invention.

FIG. 11 is a schematic diagram showing the pump cassette 202 installed in the blood pump 104 in accordance with an embodiment of the present invention. The pump cassette 202 is installed in the cassette receptacle 704. The door assembly 402 will only close if the pump cassette 202 is oriented correctly in the cassette receptacle 704, and will not close if the pump cassette 202 is inserted backwards so that the tubing connected to the pump cassette 202 does not align with corresponding channels in the door latch 703. When the door assembly 402 is closed and the bladder in the door assembly 402 is inflated, the pump cassette 202 is pressed tightly against the bezel gasket 612 and gasket retainer 614 on the front panel assembly 408, the RBCC inlet tube 204 is captured by the air-in-line sensor 610 on the front plate assembly 408, the occluder blade 813 aligns with and occludes the working solution distribution tube 212, and the occluder blade 814 aligns with and occludes both the RBCC inlet tube 204 and the incubation solution outlet tube 206.

Blood Processing

As discussed above, the compounder 102 and the blood pumps 104 operate under control of the process controller 120. In exemplary embodiments of the present invention, introduction of the anti-pathogen compound into the RBCC is performed in two stages, a first stage in which the anti-pathogen compound is mixed with buffer solution to a first concentration to form the working solution, and a second stage in which the working solution is mixed with the RBCC to a second concentration to form the incubation solution. The two-stage process is described in more detail in Application D72.

Figure 12:
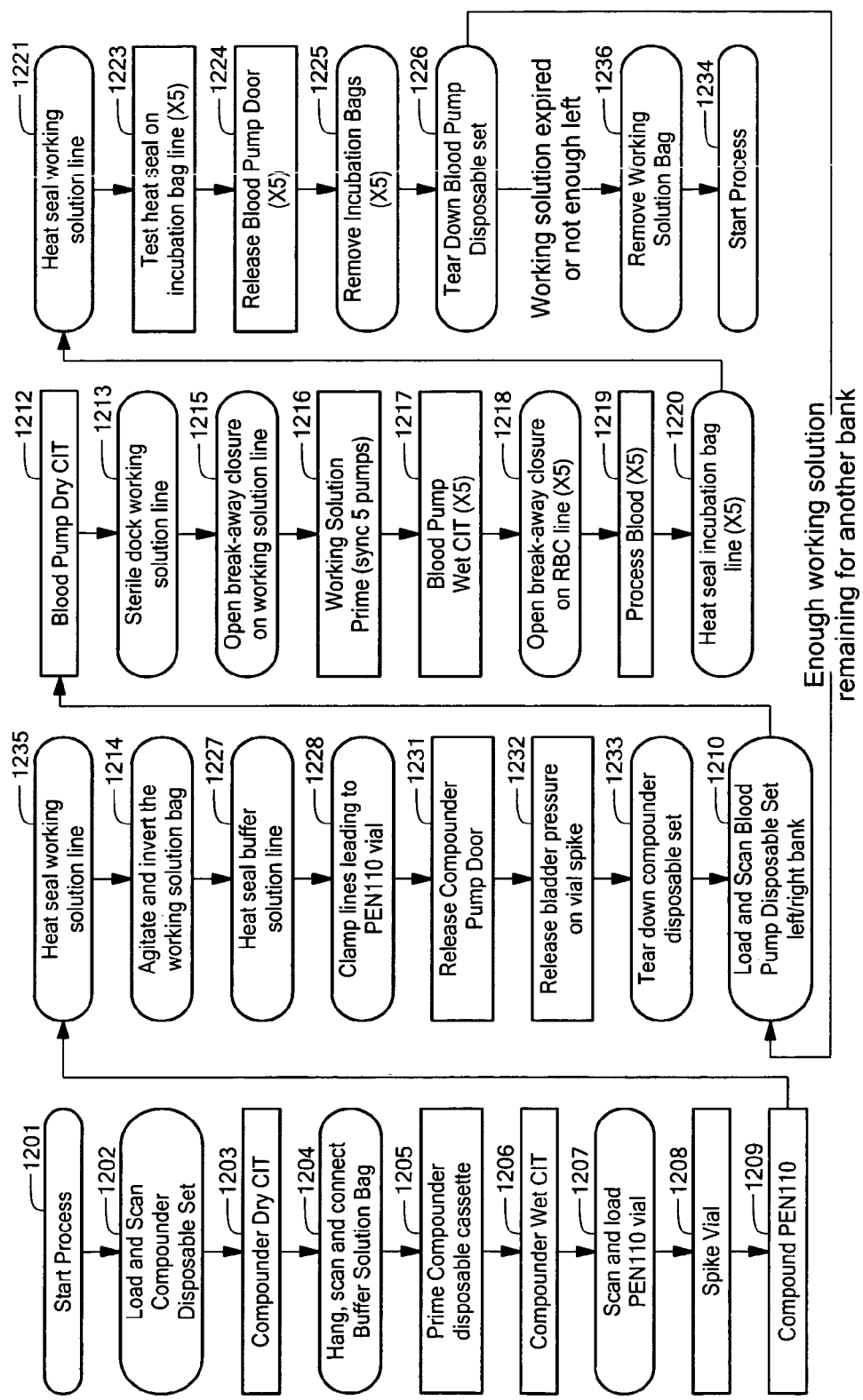
FIG. 12 shows a process flow diagram describing the compounding and blood treatment process, which is coordinated by the process controller, in accordance with an embodiment of the present invention.

FIG. 12 shows a process flow diagram describing the compounding and blood treatment process, which is coordinated by the process controller 120, in accordance with an embodiment of the present invention. Rectangular blocks indicate commands sent to the pump by the process controller 120. Rounded blocks indicate instructions sent to the operator by the process control 120.

The process starts in block 1201. In block 1202, the process controller instructs the operator to load and scan a compounder disposable set. After the compounder disposable set is loaded into the compounder, the process controller instructs the compounder to run a dry cassette integrity test (CIT) in block 1203. Assuming the dry CIT is acceptable, the process controller instructs the operator to hang, scan, and connect the buffer solution bag so that the buffer solution bag is connected to the inlet port of the pump cassette, in block 1204. The process controller then instructs the compounder to prime the compounder disposable set, in block 1205. The process controller then instructs the compounder to run a wet CIT, in block 1206. Assuming the wet CIT is acceptable, the process controller then instructs the operator to scan and load the vial assembly and spike receptacle into the vial spike assembly, in block 1207. The process controller then instructs the compounder to spike the vial, in block 1208. Once spiking is completed, the process controller instructs the compounder to perform the compounding operation, in block 1209. Compounding is described in more detail in Application D70.

After compounding is complete, the process controller coordinates "teardown" of the compounder for removal and disposal of the compounder disposable set from the compounder. Specifically, with reference again to FIG. 12, the process controller instructs the operator to heat seal the working solution line, in block 1235, and then agitate and invert the working solution bag, in block 1214. The process controller then instructs the operator to heat seal the buffer solution line, in block 1227. The process controller then instructs the operator to clamp the lines leading to the vial, in block 1228. The process controller then instructs the compounder to release the compounder door, in block 1231, which is accomplished by deflating the bladder in the door assembly. The process controller then instructs the compounder to release the bladder pressure on the vial spike (piston), in block 1232. The process controller then instructs the operator to remove the compounder disposables from the compounder 1233.

After compounder "teardown" is complete, the process controller coordinates the blood processing operations in which the RBCC is mixed with working solution by the blood pumps 104 in order to produce the incubation solutions. Specifically, in block 1210, the process controller 120 instructs the operator to load and scan a blood disposables set in one of the banks of blood pumps 104. The process controller 120 may instruct the operator to scan, for each blood pump, the RBCC bag 106, the blood pump 104, and the incubation bag 118. The process controller 120 stores this information so that there is a correlation between each blood pump 104 and the solutions processed and produced by it. This information can be used, for example, to identify all incubation solutions produced by a particular blood pump 104 if the blood pump 104 is found to be defective.

After the blood disposables set is loaded, the process controller 120 instructs the blood pumps 120 to perform a dry CIT, in block 1212. The dry CIT operation is described in more detail with reference to FIG. 14 below. Assuming the dry CIT is successful, the process controller 120 then instructs the operator to connect the working solution inlet tube 210 of the blood disposables set to the working solution bag 112 using the sterile dock 114, in block 1213, and open the break-away closure on the working solution inlet tube 210, in block 1215. The process controller 120 then coordinates working solution priming of the blood pumps 104, in block 1216, and then performs a wet CIT on each of the blood pumps 104, in block 1217. The priming and wet CIT operations are described in more detail respectively with reference to FIGS. 15 and 16 below. Assuming the wet CIT is successful, the process controller 120 instructs the operator to open the break-away closures on the RBCC inlet tubes 204, in block 1218. These break-away closures are not opened earlier in order to prevent contamination of the blood in case of a blood pump failure.

After the break-away closures are opened, the process controller 120 instructs the blood pumps 104 to mix the RBCC with the working solution to produce the incubation solutions, in block 1219. The blood mixing operation is described in more detail with reference to FIG. 17 below.

After blood mixing is complete, the process controller 120 instructs the operator to heat seal the incubation solution outlet tubes 206, in block 1220, and to heat seal the working solution distribution tubes 212, in block 1221. The process controller 120 then instructs the blood pumps 104 to test the heat seal on the incubation solution outlet tubes 206, in block 1223. Assuming the tubes are sealed, the process controller 120 instructs the blood pumps 104 to release their respective doors, in block 1224. The process controller 120 then instructs the operator to remove the incubation bags 118, in block 1225, and to tear down the blood disposables set, in block 1226.

If there is enough working solution remaining for another blood processing cycle, then the process may recycle to block 1210 to coordinate blood processing operations for another bank of blood pumps. If and when the working solution has expired or there is not enough working solution remaining for another blood processing cycle, then the process controller typically instructs the operator to remove the working solution bag, in block 1236. The process ends in block 1234.

Figure 13A:
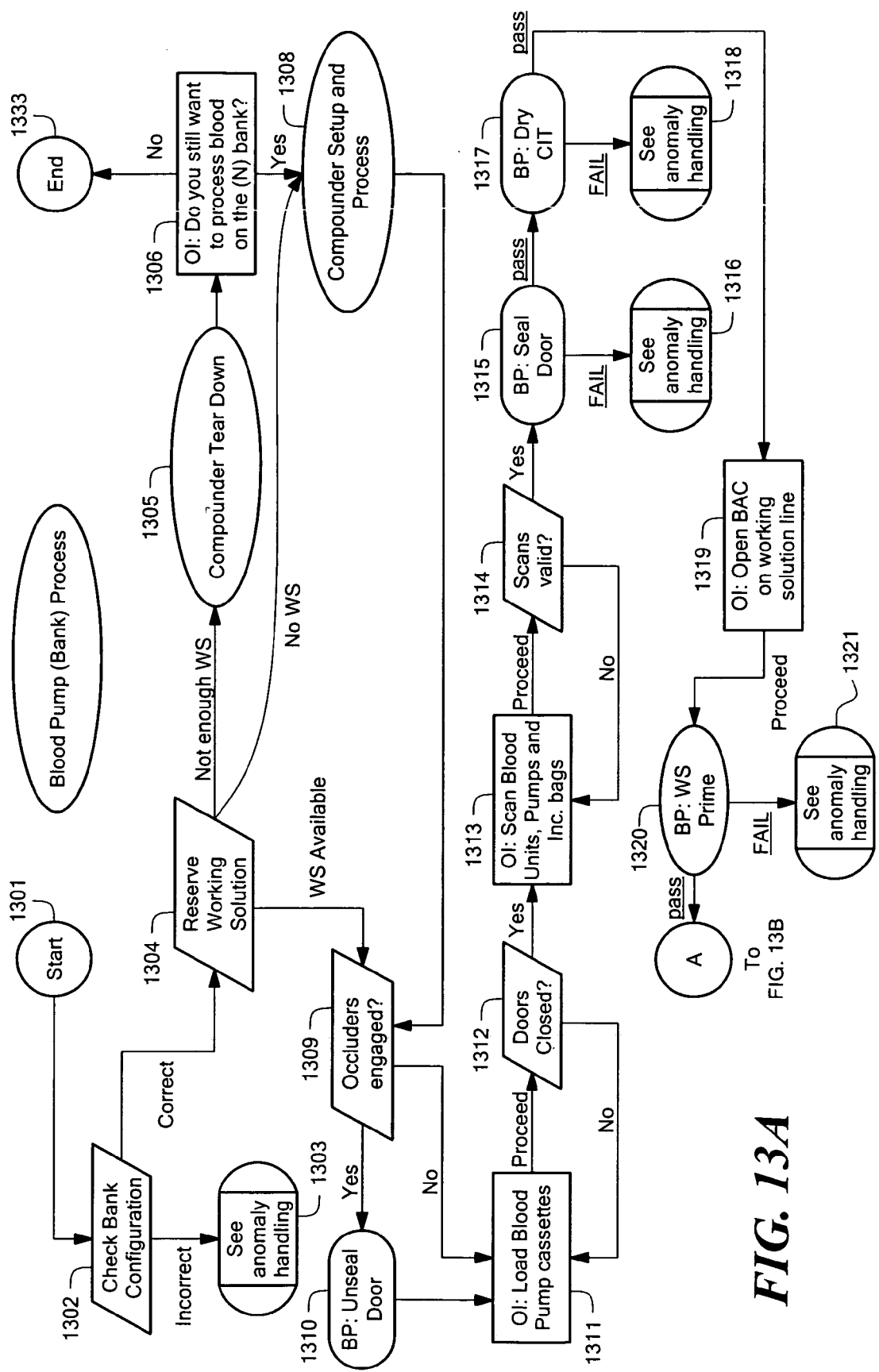
FIGS. 13A-B show a process flow diagram showing additional details of the blood processing operations in accordance with an embodiment of the present invention.
Figure 13B:
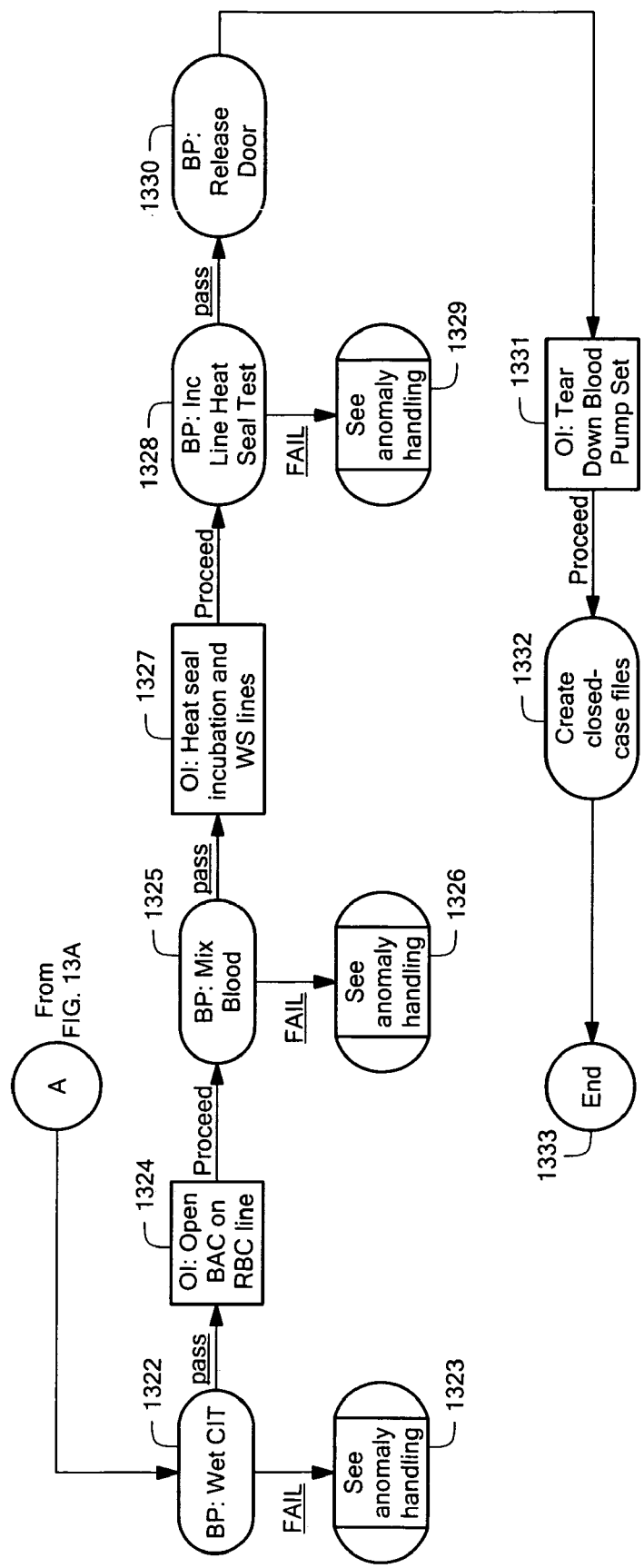

FIGS. 13A-B show a process flow diagram showing additional details of the blood processing operations in accordance with an embodiment of the present invention. The process begins in block 1301. A check is first made to confirm that the bank of blood pumps 104 is configured properly, in block 1302. This involves, among other things, confirming that there is communication between the process controller 120 and the five blood pumps 104, confirming that all five blood pumps 104 are configured to operate as blood pumps, and confirming that all five blood pumps 104 contain the correct version of embedded software. The process enters anomaly handling, in block 1303, if the bank is not configured properly.

If the bank is configured properly, then a determination is made as to whether there is a sufficient quantity of working solution and a sufficient amount of time for performing the blood processing operation, in block 1304. If there is no working solution, then the compounder setup and process operation is performed as described in Application D70, in block 1308. If there is an insufficient amount of working solution, then the compounder teardown operation is performed as described in Application D70, in block 1305, and, in block 1306, the operator is given the option to either terminate the blood processing operation, in which case the process ends in block 1333, or continue the blood processing operation, in which case the compounder setup and process operation is performed as described in Application D70, in block 1308.

If there is a sufficient quantity of working solution in block 1304, or after working solution is prepared in block 1308, the blood disposables set is loaded into the blood pumps 104. If the occluders are engaged, in block 1309, then the door is unsealed, in block 1310. Once the door is unsealed, the operator is instructed to load the blood disposables set, in block 1311, and to close the door. When the door is confirmed to be closed, in block 1314, the operator is instructed to scan the RBCC bags, blood pumps, and incubation solution bags, in block 1313. When scanning is complete, in block 1314, the blood pumps 104 are instructed to seal their respective doors, in block 1315. If a door is unable to be sealed, then the process enters anomaly handling, in block 1316, which typically includes instructing the operator to reload the pump cassette.

If the door is able to be sealed, then the blood pumps 104 are instructed to perform the dry CIT, in block 1317. If the dry CIT fails, then the process enters anomaly handling, in block 1318, which typically involves instructing the operator to reload the pump cassette and running the dry CIT again. If the dry CIT passes, then the operator is instructed to connect the working solution inlet tube 210 to the working solution bag 112 using the sterile dock and to open the break-away closure on the working solution line, in block 1319. The blood pumps 104 are then instructed to perform the priming process, in block 1320. If the priming process fails, then the process enters anomaly handling, in block 1320. If priming is successful, then the blood pumps 104 are instructed to perform the wet CIT, in block 1322. If the wet CIT fails, then the process enters anomaly handling, in block 1323. If the wet CIT passes, then the operator is instructed to open the break-away closures on the RBCC inlet tubes, in block 1324. The blood pumps 104 are then instructed to mix the RBCC and the working solution to form incubation solution, in block 1325. If there is a failure during mixing, then the process enters anomaly handling, in block 1326.

Assuming blood processing is successful, the operator is instructed to heat seal the incubation and working solution lines, in block 1327. The blood units 104 are then instructed to test the seal on the incubation line, in block 1328. If the test fails, then the process enters anomaly handling, in block 1329.

Assuming the incubation line is sealed, then the blood pumps 104 are instructed to release their respective doors, in block 1330, after which the operator is instructed to teardown the blood disposables set, in block 1331. A closed-case file is prepared, in block 1332. The process ends in block 1333.

Blood Pump Dry Cassette Integrity Test

The dry cassette integrity test (CIT) is used to identify air leaks in the cassette membranes prior to pumping any fluids. Identifying a cassette with a membrane hole will protect the RBCC from being contaminated by a potentially non-sterile cassette, and will reduce the potential of pumping fluid into the blood unit itself. Also, at the time of the dry CIT, an internal pressure transducer calibration check is performed in order to ensure that none of the transducers have failed or drifted out of calibration. Also during the dry CIT, the fluid valve leading to the air vent on the cassette is tested by closing the valve, pressurizing the pump chamber, and observing the pressure decay.

Figure 14:
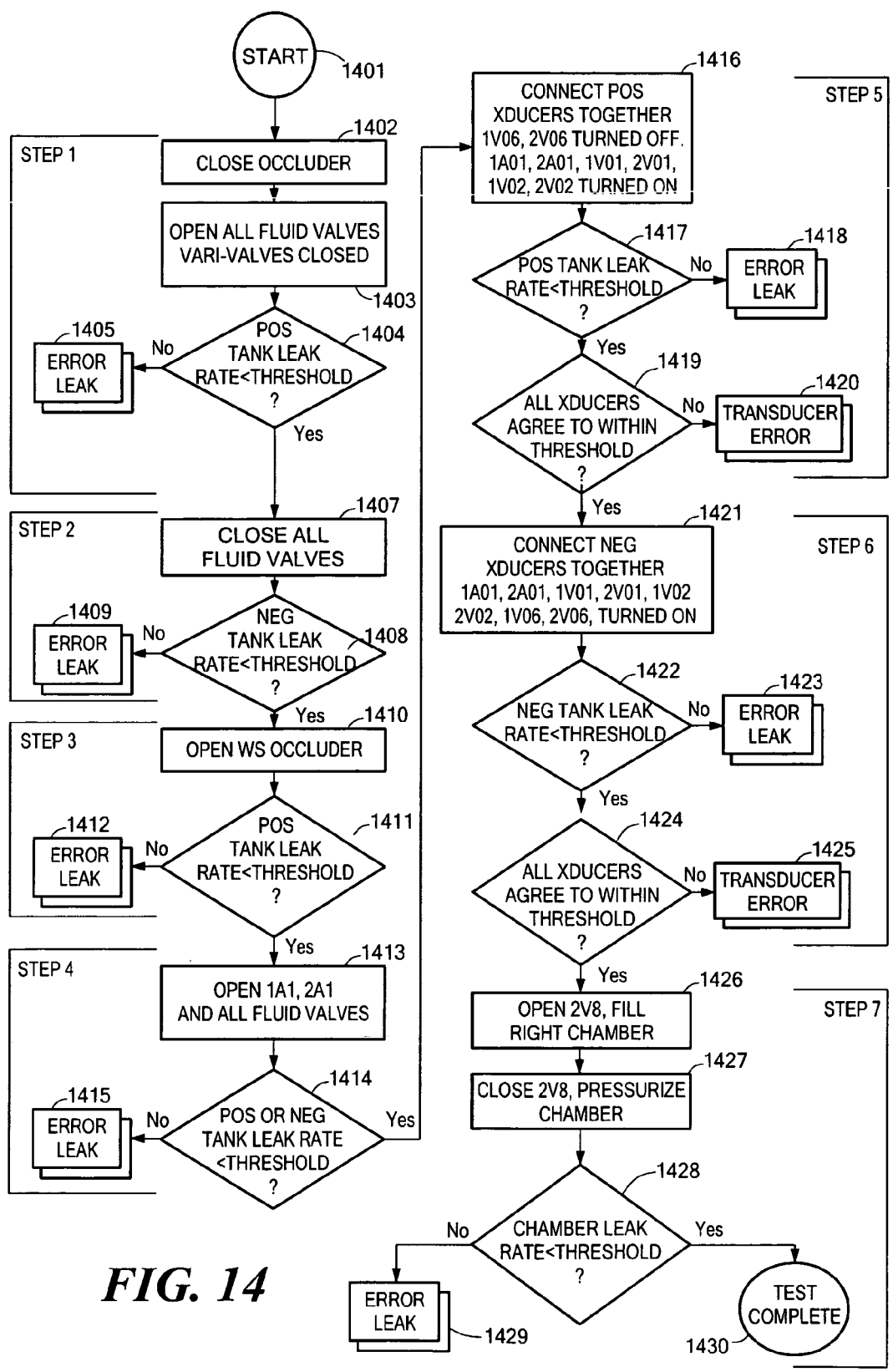
FIG. 14 shows a process flow diagram describing the blood pump dry CIT process in accordance with an embodiment of the present invention.

FIG. 14 shows a process flow diagram describing the blood pump dry CIT process in accordance with an embodiment of the present invention. The dry CIT process begins in block 1401. The positive pneumatic system is first isolated from the cassette and a baseline leak rate for the positive assembly is obtained, specifically by closing the working solution line occluder 813, in block 1402, opening all fluid valves and closing the variable valves, in block 1403, measuring the positive tank leak rate, in block 1404, and generating an error signal if the positive tank leak rate is greater than or equal to the predetermined threshold, in block 1405.

Then, the negative pneumatic system is isolated from the cassette and a baseline leak rate for the negative assembly is obtained, specifically by closing all fluid valves, in block 1407, measuring the positive tank leak rate, in block 1408, and generating an error signal if the negative tank leak rate is greater than or equal to a predetermined threshold, in block 1409.

Then, the process tests the cassette sheeting of the valves outside of the volcano valves, specifically by opening the working solution line occluder 813, in block 1410, measuring the positive tank leak rate, in block 1411, and generating an error signal if the positive tank leak rate is greater than or equal to a predetermined threshold, in block 1412.

Then, the process tests the cassette sheeting at the center of the volcano valves, specifically by opening valves 1A1 and 2A1 and all fluid valves, in block 1413, measuring the positive and negative tank leak rates, in block 1414, and generating an error signal if the positive or negative tank leak rate is greater than or equal to a predetermined threshold, in block 1415.

Then, the process verifies calibration of the positive transducers, specifically by isolating the positive transducers and connecting the positive transducers together, in block 1416, measuring the positive tank leak rate, in block 1417, generating an error signal if the positive tank leak rate is greater than or equal to a predetermined threshold, in block 1418, determining whether all positive transducers agree to within a predetermined threshold, in block 1419, and generating an error signal if the positive transducers do not agree to within a predetermined threshold, in block 1420.

Then, the process verifies calibration of the negative transducers, specifically by isolating the negative transducers and connecting the negative transducers together, in block 1421, measuring the negative tank leak rate, in block 1422, generating an error signal if the negative tank leak rate is greater than or equal to a predetermined threshold, in block 1423, determining whether all negative transducers agree to within a predetermined threshold, in block 1424, and generating an error signal if the negative transducers do not agree to within a predetermined threshold, in block 1425.

Finally, the process tests integrity of the fluid valve leading to the vent filter, specifically by filling the chamber, in block 1426, pressurizing the chamber, in block 1427, measuring the chamber leak rate, in block 1428, and generating an error signal if the chamber leak rate is greater than or equal a predetermined threshold, in block 1429. The dry CIT process ends in block 1430.

Blood Pump Priming

The working solution priming process operates on an entire bank of five blood pumps, where all blood pumps share a single working solution line. The working solution priming process is coordinated by the process controller 120 so as to prevent one pump from drawing in air that is being expelled by another pump, specifically by priming the operating the blood pumps symmetrically from the middle blood pump outward. Each blood pump is responsible for detecting "no flow" conditions during priming and also for detecting air in the working solution chamber of the pump cassette 202 after the priming operation is complete. The priming process uses two operations, namely a "put" operation and a "get" operation. The "put" operation involves pumping the contents of the working solution chamber of the pump cassette 202 (air and/or working solution) out through the working solution inlet 304 to the working solution bag, specifically by applying a positive pressure to the working solution chamber. The "get" operation involves drawing from the working solution inlet 304, specifically by applying a negative pressure to the working solution chamber. For convenience, the five blood pumps 104 in a bank are referred to numerically from one to five, where pump three is the middle pump of the bank, pumps two and four are the pumps adjacent to the middle pump, and pumps one and five are the outside pumps.

Figure 15:
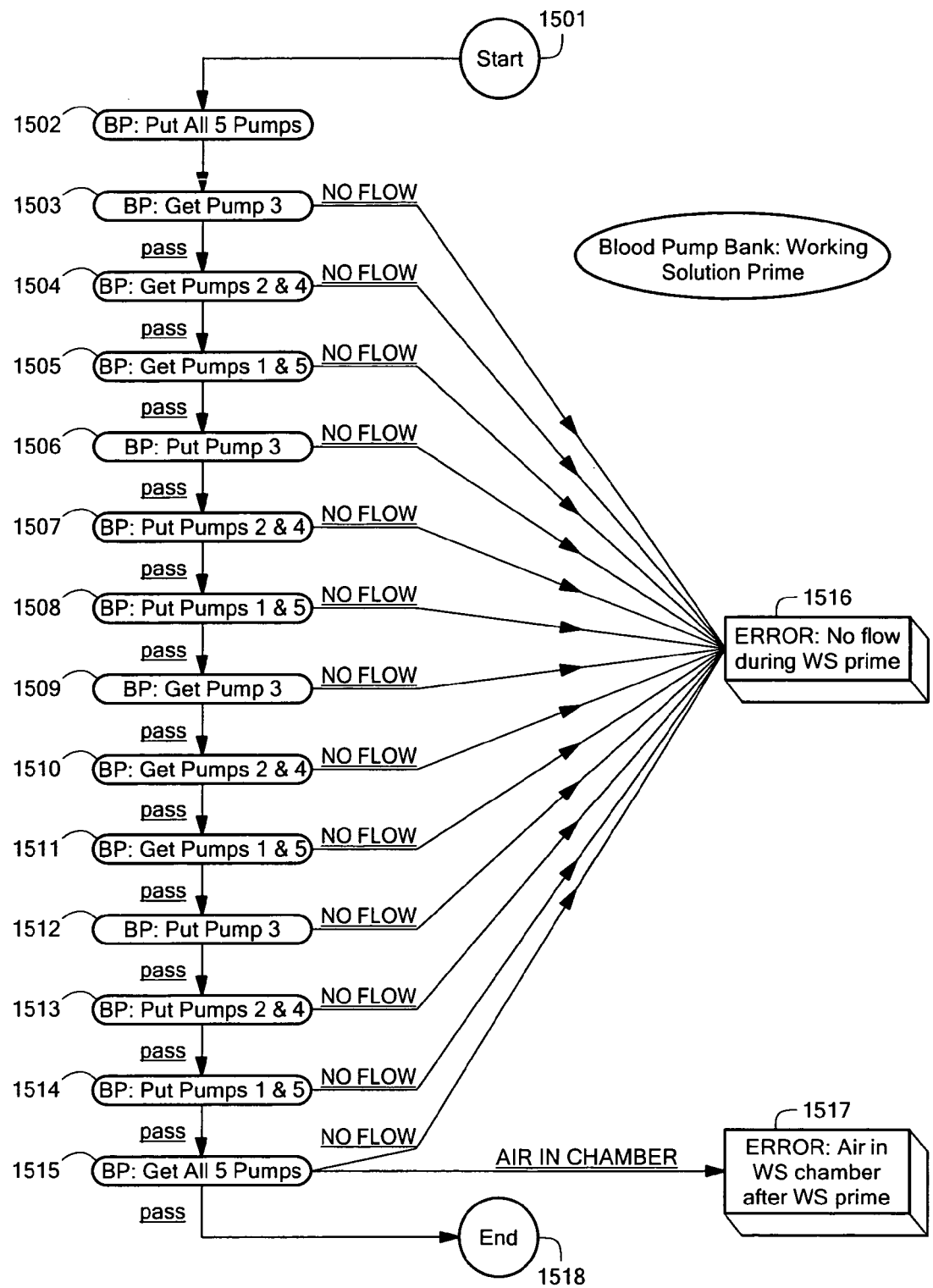
FIG. 15 shows a process flow diagram describing the blood pump working solution priming process in accordance with an embodiment of the present invention.

FIG. 15 shows a process flow diagram describing the blood pump working solution priming process in accordance with an embodiment of the present invention. The priming process begins in block 1501. In block 1502, a put operation is performed on all five blood pumps. This removes as much air as possible from the working solution chambers of the pump cassettes 102. Then, get operations are performed on the blood pumps, starting with pump three, in block 1503, then pumps two and four simultaneously, in block 1504, and then pumps one and five simultaneously, in block 1505. Then, put operations are performed on the blood pumps, starting with pump three, in block 1506, then pumps two and four simultaneously, in block 1507, and then pumps one and five simultaneously, in block 1508. Then, get operations are performed on the blood pumps, starting with pump three, in block 1509, then pumps two and four simultaneously, in block 1510, and then pumps one and five simultaneously, in block 1511. Then, put operations are performed on the blood pumps, starting with pump three, in block 1512, then pumps two and four simultaneously, in block 1513, and then pumps one and five simultaneously, in block 1514. Finally, get operations are performed on all five pumps simultaneously, in block 1518. If a blood pump detects a "no flow" condition during any of the get and put operations, an error condition is raised in block 1516, and priming is terminated. If a blood pump detects air in the working solution chamber after completion of the priming process, then an error condition is raised in block 1517. The priming process ends in block 1518.

Blood Pump Wet Cassette Integrity Test

The wet cassette integrity test (CIT) is used to identify defects within the injection-molded body of the cassette. The wet CIT involves testing the functionality of all of the fluid valves within the cassette as well as testing for "cross-talk" between the fluid paths and fluid pump chambers within the cassette. The wet CIT is performed on a partially primed cassette, after priming the working solution pump chamber, but before priming the RBC pump chamber. Therefore, a complete wet CIT is performed on the working solution pump chamber, but the RBC pump chamber is tested using air pressure and decay. Priming and wet testing of the RBC pump chamber is performed during blood mixing, as discussed below.

Figure 16:
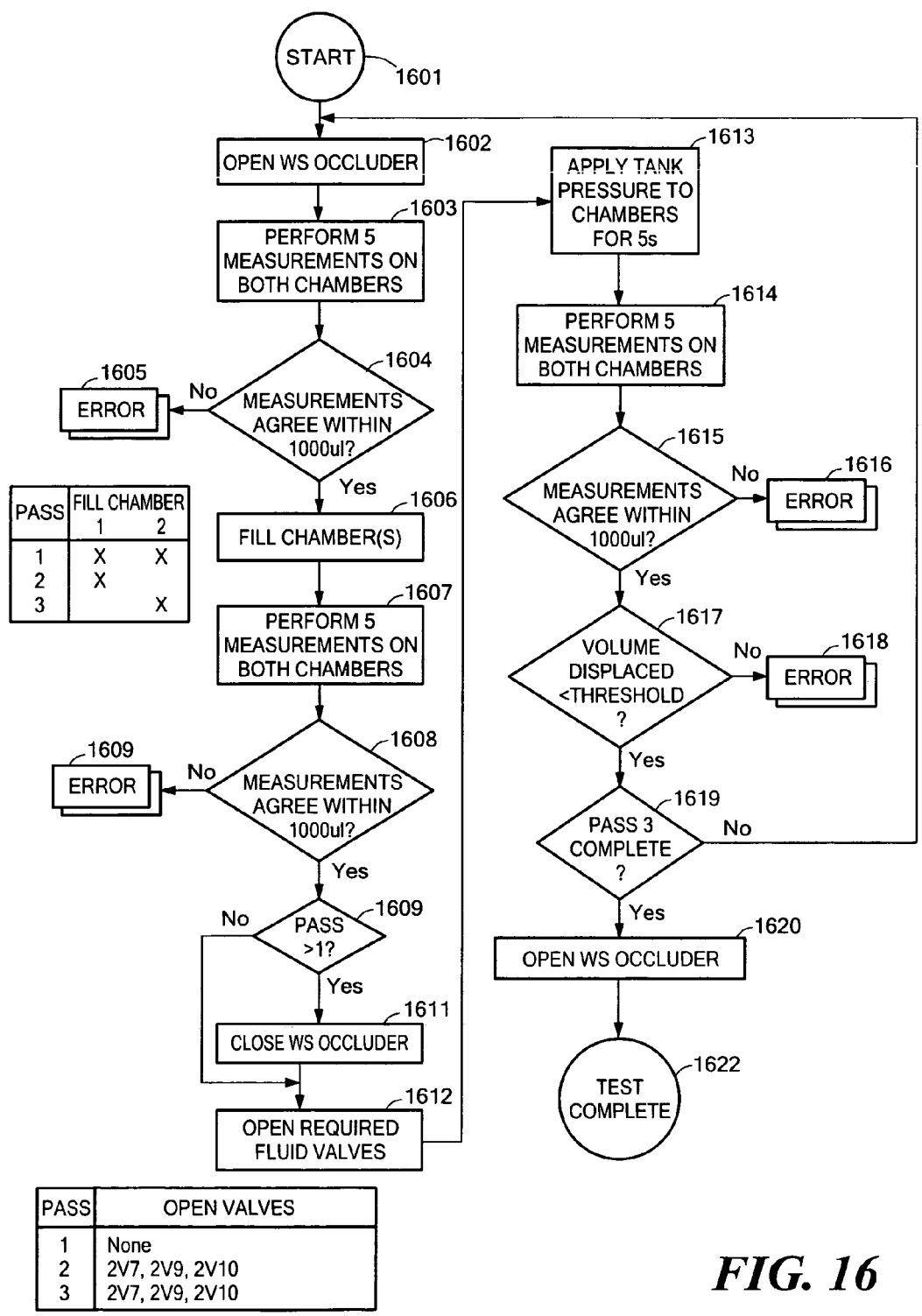
FIG. 16 shows a process flow diagram describing the blood pump wet CIT process in accordance with an embodiment of the present invention.
Figure 17A:
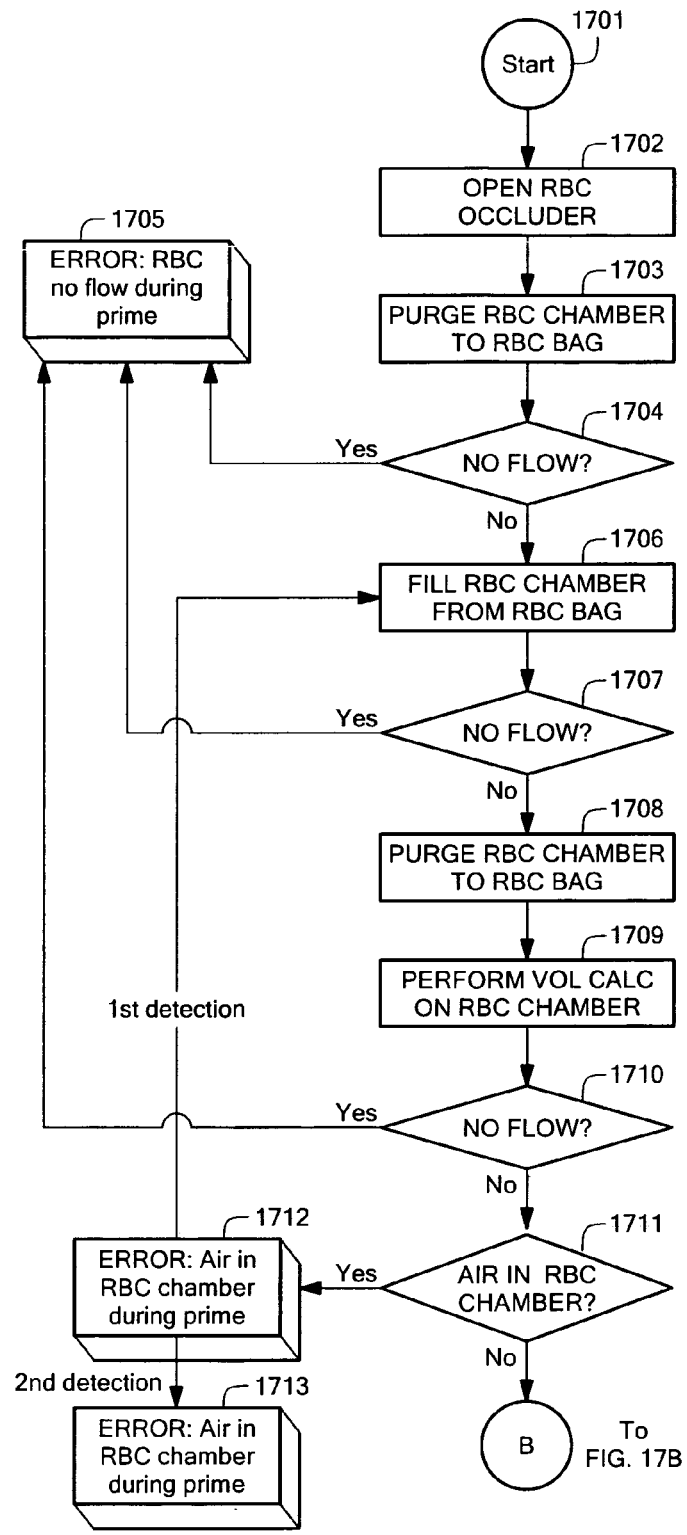
FIGS. 17A-D show a process flow diagram describing the blood mixing process in accordance with an embodiment of the present invention.
Figure 17B:
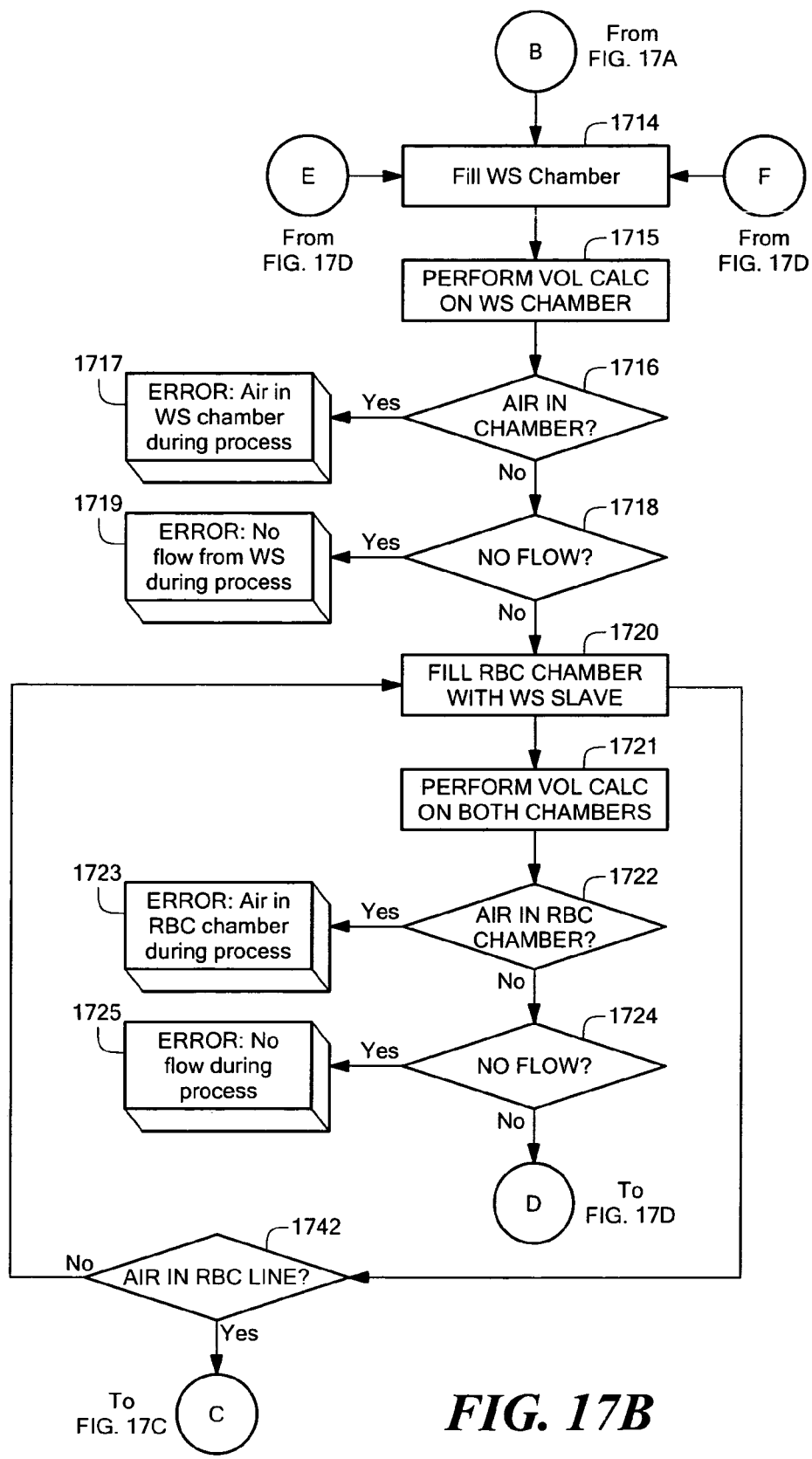
Figure 17C:
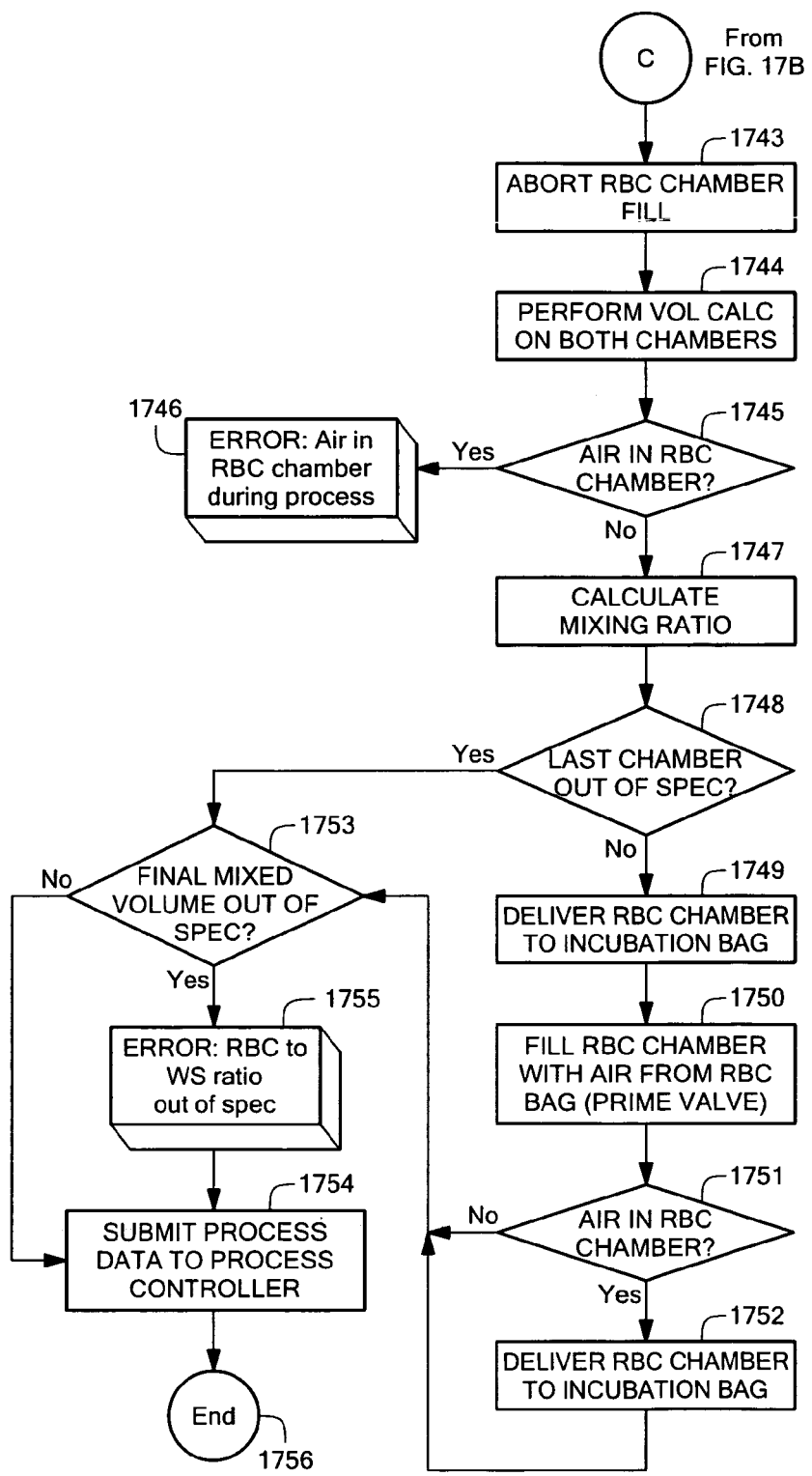
Figure 17D:
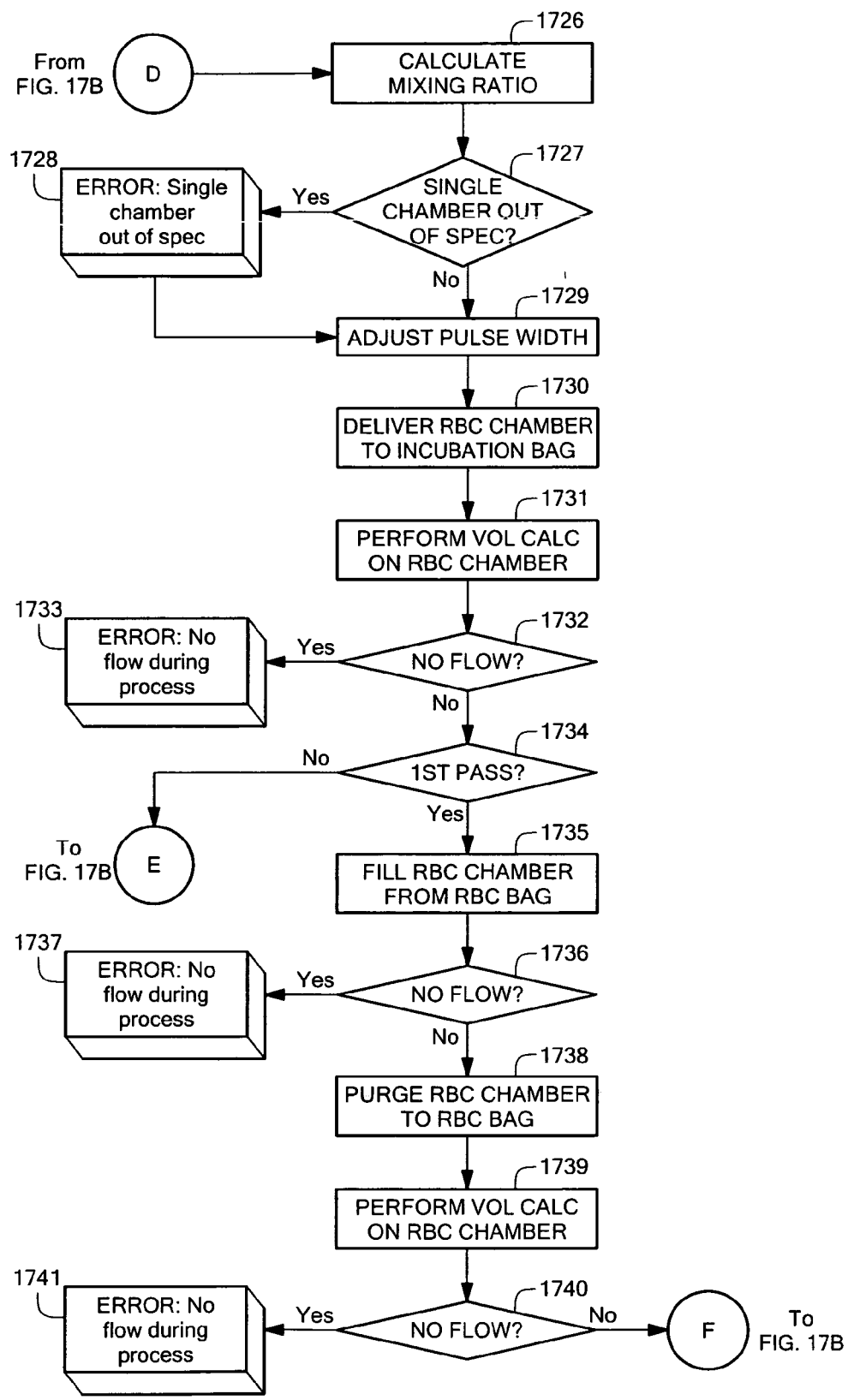

FIG. 16 shows a process flow diagram describing the blood pump wet CIT process in accordance with an embodiment of the present invention. The wet CIT process begins in block 1601, and involves three passes of blocks 1602 through 1619. In each pass, the working solution line occluder 813 is retracted, in block 1602, and various measurements are performed on both chambers, in block 1603. If the measurements are outside of a predetermined threshold (NO in block 1604), then an error signal is generated, in block 1605. Otherwise, a chamber filling operation is performed, in block 1606. During the first pass, both chambers are filled; during the second pass, only one chamber is filled; during the third pass, only the other chamber is filled. After the chamber filling operation, various measurements are performed on the chambers, in block 1607. If the measurements are outside of a predetermined threshold (NO in block 1608), then an error signal is generated, in block 1609. At this point, the working solution line occluder 813 is left retracted during the first pass, but is closed during the second and third passes, in blocks 1610 and 1611. The required fluid valves are then opened, in block 1612, tank pressure is applied to the chambers for a predetermined amount of time, in block 1613, and various measurements are performed on the chambers, in block 1614. If the measurements are outside of a predetermined threshold (NO in block 1615), then an error signal is generated in block 1616. Otherwise, the process determines whether the volume displaced is within some threshold, in block 1617. If not, then an error signal is generated, in block 1618. After all three passes are complete, the working solution line occluder 813 is opened, in block 1620, and both chambers are purged to the working solution bag, in block 1621. The process ends in block 1622.

Blood Mixing

The blood mixing process is performed essentially in three stages, namely a priming stage, a mixing stage, and a residuals stage. The priming stage involves priming the RBC pump chamber 334 from the RBCC bag 106. The mixing stage involves repetitively drawing a quantity of working solution in to the working solution pump chamber 333 and drawing a quantity of RBCC through the channel 310 into the RBC pump chamber 334 while pulsing working solution from the working solution pump chamber 333 into the channel 310 so that the working solution and RBCC mix within the channel 310 and the RBC pump chamber 334. The pulsing of working solution is dynamically adjusted so that the resulting incubation solution has a predetermined concentration of working solution, within certain limits. The mixing stage continues until air is detected in the RBCC inlet tube 204 by the air-in-line sensor 610, signaling that there is no more RBCC to be processed. The residuals stage handles the residual contents in the RBC pump chamber 334 (if any) following the mixing stage. In the residuals stage, the concentration of working solution and RBCC in the RBC pump chamber 334 is measured, and the contents of the RBC pump chamber 334 are delivered to the incubation bag 118 if and only if the concentration of working solution and RBCC is within a predetermined specification. The overall concentration of working solution in the incubation solution is also measured, and a signal is generated to indicate whether or not the incubation solution is usable. The blood mixing process preferably prevents fluid from being pushed back into the working solution line after RBCC has been introduced into the pump cassette in order to prevent contamination of the working solution.

FIGS. 17A-D show a process flow diagram describing the blood mixing process in accordance with an embodiment of the present invention. The process begins in block 1701, and proceeds to prime the RBC pump chamber 334. Specifically, the RBC occluder 814 is opened, in block 1702, and the contents of the RBC pump chamber 334 are purged to the RBCC bag 106, in block 1703. If a no flow condition is detected in block 1704, then the process ends in failure in block 1705. Otherwise, the RBC pump chamber 334 is filled from the RBCC bag 106, in block 1706. If a no flow condition is detected in block 1707, then the process ends in failure in block 1705. Otherwise, the contents of the RBC pump chamber 334 is purged back to the RBCC bag 106, in block 1708, and the volume of the RBC pump chamber 334 is computed, in block 1709. If a no flow condition is detected in block 1710, then the process ends in failure in block 1705. If air is detected in the RBC pump chamber 334 in block 1711, then an error signal is generated, in block 1712, and a second attempt is made to prime the RBC pump chamber 334 by repeating blocks 1706 through 1711. If air is again detected in the RBC pump chamber 334 in block 1711, then the process ends in failure in block 1713.

If the RBC pump chamber 334 is successfully primed, then the process continues with the mixing stage. Specifically, the working solution pump chamber 333 is filled from the working solution bag 112 with working solution, in block 1714. The volume of the working solution pump chamber 333 is measured, in block 1715. If air is detected in the working solution pump chamber 333 in block 1716, then the process ends in failure in block 1717. If a no flow condition is detected in block 1718, then the process ends in failure in block 1719.

The RBCC is then mixed with working solution, in block 1720, specifically by drawing RBCC from the RBCC bag 106 through the channel 310 into the RBC pump chamber 334 while simultaneously pulsing working solution from the working solution pump chamber 333 into the channel 310 so that the working solution and RBCC are mixed within the channel 310 and the RBC pump chamber 334. While this mixing is being performed, the process is monitoring for air in the RBCC inlet tube 204, in block 1742. Assuming no air is detected in the RBCC inlet tube 204, in block 1742, the volumes of both chambers 333 and 334 are measured, in block 1721. If air is detected in the RBC pump chamber 334 in block 1722, then the process ends in failure in block 1723. If a no flow condition is detected in block 1724, then the process ends in failure in block 1725.

After mixing the working solution and RBCC, the concentration of working solution to RBCC in the RBC pump chamber 334 is calculated, in block 1726, and a determination is made whether the concentration for this particular chamber is within predetermined specifications, in block 1727. If the concentration of working solution to RBCC in the RBC pump chamber 334 is outside of specifications, then an error condition is signaled, in block 1728. In any case, though, the pulse width is adjusted based upon the concentration of working solution to RBCC in the RBC pump chamber 334, in block 1729, and the contents of the RBC pump chamber 334 are delivered to the incubation bag 118, in block 1730. The volume of the RBC pump chamber 1731 is measured, in block 1731. If a no flow condition is detected in block 1732, then the process ends in failure in block 1733.

In this first pass of the mixing stage, from block 1734, the RBC pump chamber 334 is filled from the RBCC bag 106, in block 1735. If a no flow condition is detected in block 1736 while attempting to fill the RBC pump chamber 334 from the RBCC bag 106 then the process ends in failure in block 1737. Otherwise, the contents of the RBC pump chamber 334 are purged to the RBCC bag 106, in block 1738, and the volume of the RBC pump chamber 334 is computed, in block 1739. If a no flow condition is detected in block 1740 while attempting to purge the contents of the RBC pump chamber 334, then the process ends in failure in block 1741. Otherwise, the mixing stage continues by recycling to block 1714 and repeating blocks 1714 through 1734. During the second and subsequent passes of the mixing stage, the process recycles from block 1734 to block 1714, omitting blocks 1735 through 1741.

When air is detected in the RBCC inlet tube 204, in block 1742, filling of the RBC pump chamber 334 with RBCC and working solution is aborted (preferably before air has entered the RBC pump chamber), in block 1743, and a volume calculation is performed for both chambers, in block 1744. If air is detected in the RBC pump chamber 334 in block 1745, then the process ends in failure in block 1746. Assuming that there is no air in the RBC pump chamber 334, then the concentration of working solution to RBCC in the RBC pump chamber 334 is calculated, in block 1747, and a determination is made whether the concentration for this particular chamber is within predetermined specifications, in block 1748. If and only if the concentration of working solution to RBCC in the RBC pump chamber 334 is within specifications, the contents of the RBC pump chamber 334 are delivered to the incubation bag 118, in block 1749, the RBC pump chamber 334 is filled from the RBCC bag 106, in block 1750, and, upon detecting air in the RBC pump chamber 334 in block 1751, the contents of the RBC pump chamber 334 are delivered to the incubation bag 118, in block 1752. Whether or not the residual contents of the RBC pump chamber 334 are delivered to the incubation bag 118, the overall concentration of working solution to RBCC in the incubation solution is calculated, in block 1753. If the overall concentration is outside of specifications, then an error condition is signaled, in block 1755. In any case, process data is sent to the process controller 120, in block 1754. The process ends in block 1755.

Manual Teardown

During normal blood pump teardown, the blood pump 104 receives commands from the process controller 120 to release pressure against the pump door so that the door can be opened by the operator. The pressure against the door comes from both the door piston bladder and the occluders. While the door piston bladder is pressurized and the tubing occluders are engaged, it is virtually impossible for the operator to open the pump door and remove the pump cassette. If communication between the process controller 120 and the blood pump 104 is lost, then the operator will need to relieve this pressure manually in order to remove the cassette. Among other things, this involves the operator pressing the manual door release valve on the back of the pump to deflate the bladder in the door assembly. The operator may also manually retract the occluders if necessary.

Figure 19:
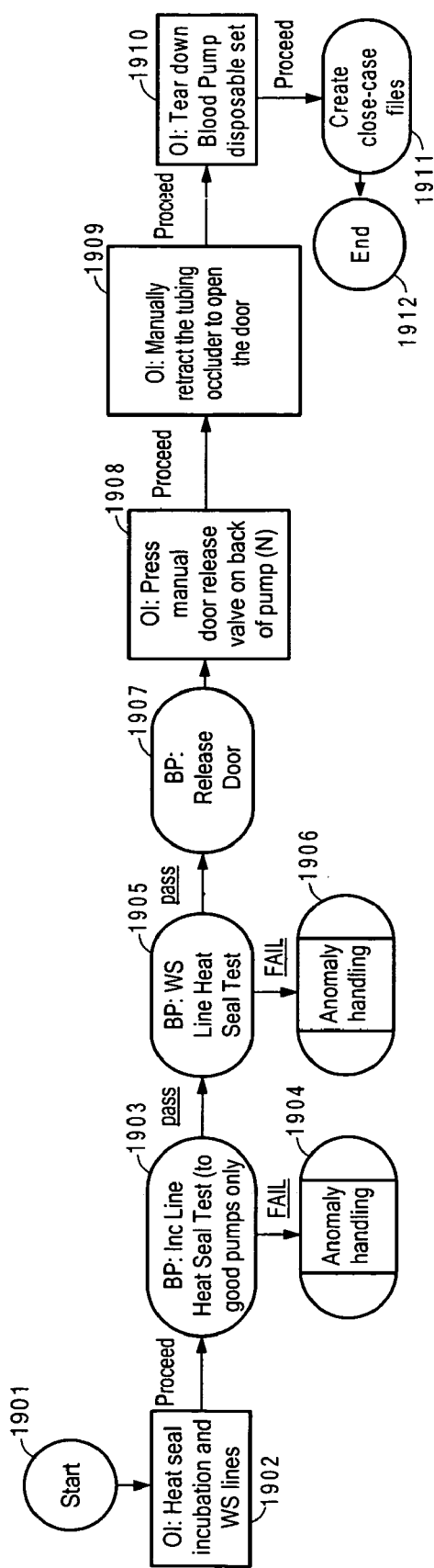
FIG. 19 shows a process flow diagram describing the process for manual blood pump teardown in accordance with an embodiment of the present invention.

FIG. 19 shows a process flow diagram describing the process for manual blood pump teardown in accordance with an embodiment of the present invention. The process starts in block 1901. The operator is instructed to heat seal the incubation and working solution lines, in block 1902. The blood pump 104 is then instructed to test the heat seal of the incubation line, in block 1903. If the incubation line is not sealed, then the process enters anomaly handling, in block 1904. Assuming the incubation line is sealed, then the blood pump 104 is instructed to test the heat seal of the working solution line, in block 1905. If the working solution line is not sealed, then the process enters anomaly handling, in block 1906. The blood pump 104 is instructed to release the door, in block 1907, and the operator is instructed to press the manual door release valve on the back of the pump to deflate the bladder in the door assembly, in block 1908, if the blood pump 104 does not release the door. The operator then manually retracts the occluders if necessary to allow opening of the door, in block 1909. The operator then removes the blood disposables, in block 1910. A close-case file is created indicating the failure, in block 1911. The process ends in block 1912.

Volumetric Calibration

The blood pump 104 is typically calibrated periodically to verify its ability to accurately measure volumes of pumped fluids. In exemplary embodiments of the invention, this calibration is done by running test measurements with two different test cassettes having different but known chamber volumes.

Figure 18:
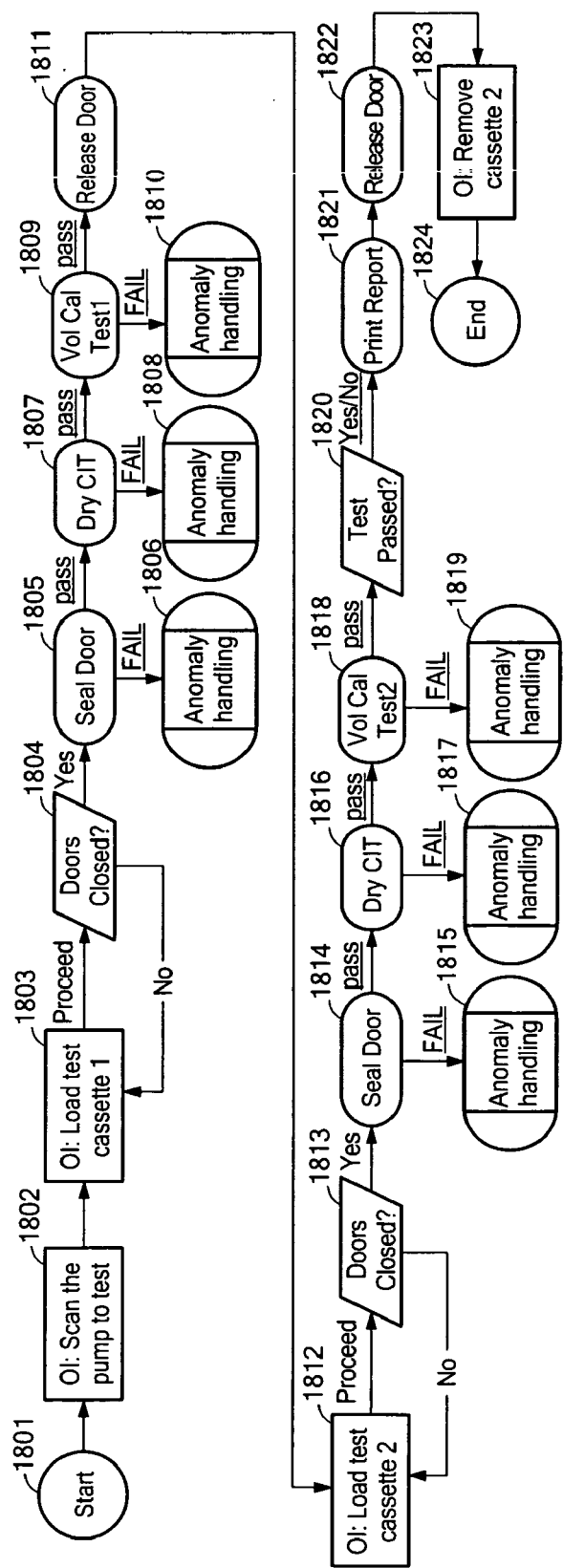
FIG. 18 shows a process flow diagram describing the volumetric calibration process in accordance with an embodiment of the present invention.

FIG. 18 shows a process flow diagram describing the volumetric calibration process in accordance with an embodiment of the present invention. The process begins in block 1801. The operator is instructed to scan a bar code on the blood pump 104 in block 1802 in order to test the blood pump 104. The operator is then instructed to load the first test cassette, in block 1803. Upon confirmation that the door is closed, in block 1804, the door is sealed, in block 1805. If the door fails to seal properly, then the process enters anomaly handling, in block 1806. If the door seals properly, a dry CIT is run, in block 1807. If the dry CIT fails, then the process enters anomaly handling, in block 1808. If the dry CIT passes, then a volume calibration test is run to measure the volume of the chambers, in block 1809. If the difference between the measured volume and the known volume of the first cassette is greater than or equal to some predetermined threshold, then the process enters anomaly handling, in block 1810. Otherwise, the door is released, in block 1811, and the operator is instructed to load the second test cassette, in block 1812. Upon confirmation that the door is closed, in block 1813, the door is sealed, in block 1814. If the door fails to seal properly, then the process enters anomaly handling, in block 1815. If the door seals properly, a dry CIT is run, in block 1816. If the dry CIT fails, then the process enters anomaly handing; in block 1817. If the dry CIT passes, then a volume calibration test is run to measure the volume of the chambers, in block 1818. If the difference between the measured volume and the known volume of the second cassette is greater than or equal to some predetermined threshold, then the process enters anomaly handling, in block 1819. Otherwise, a test pass determination is made, in block 1820, and a report is printed, in block 1821. The door is released, in block 1822, and the operator is instructed to remove the second test cassette, in block 1823. The process ends in block 1824.

It should also be noted that the flow diagrams are used herein to demonstrate various aspects of the invention, and should not be construed to limit the present invention to any particular flow or implementation. In some cases, certain process steps can be omitted or performed in a different order than shown without changing the overall results or otherwise departing from the true scope of the invention.

The present invention may be embodied in other specific forms without departing from the true scope of the invention. The described embodiments are to be considered in all respects only as illustrative and not restrictive.

What is claimed is:

1. A method for mixing a first liquid with a second liquid, the method comprising:
    actuating a first pump chamber of a membrane pumping apparatus by applying fluid pressure to the membrane to pump a first liquid into the first pump chamber through a channel of the membrane pumping apparatus; and
    actuating a second pump chamber of the membrane pumping apparatus by applying fluid pressure to the membrane to pump a quantity of a second liquid from the second pump chamber into one of the channel and the first pump chamber so as to mix the first liquid and the second liquid within the first pump chamber.

2. A method according to claim 1, wherein the second pump chamber is actuated by applying fluid pressure to the membrane to pump the second liquid into one of the channel and the first pump chamber during said pumping of the first liquid.

3. A method according to claim 1, wherein the membrane pumping apparatus is a pump cassette having pneumatically operated first and second pump chambers and a plurality of pneumatically operated valves, and wherein actuating the first and second pump chambers comprising:
    pneumatically operating the pump chambers and the valves.

4. A method according to claim 1, wherein actuating the second pump chamber to pump the quantity of the second liquid comprising:
    actuating the second pump chamber by applying fluid pressure to the membrane in a pulsatile mode.

5. A method according to claim 4, wherein the pulsatile mode is characterized by a pulse width and pulse interval, and wherein the method further comprising:
    determining a concentration of first liquid and second liquid in the first pump chamber; and
    dynamically adjusting at least one of the pulse width and pulse interval based on the concentration of first liquid and second liquid in the first pump chamber.

6. A method according to claim 5, further comprising:

actuating the second pump chamber by applying fluid pressure to the membrane to pump a second quantity of the second liquid from the second pump chamber into one of the channel and the first pump chamber using at least one of the dynamically adjusted pulse width and the dynamically adjusted pulse interval.

7. A method according to claim 1, further comprising:

actuating the first pump chamber by applying fluid pressure to the membrane to pump the contents of the first pump chamber to a receptacle.

8. A method according to claim 7, wherein the receptacle is external to the membrane pumping apparatus.

9. A method according to claim 1, wherein the first pump chamber receives the first liquid from a first liquid container external to the membrane pumping apparatus.

10. A method according to claim 1, further comprising:

prior to actuating the second pump chamber by applying fluid pressure to the membrane to pump the quantity of the second liquid from the second pump chamber, actuating the second pump chamber by applying fluid pressure to the membrane to pump second liquid into the second pump chamber from a second liquid container.

11. A method according to claim 10, wherein the second liquid container is external to the membrane pumping apparatus.

* * * * *